United States Patent [19]

Bayer et al.

[11] 4,093,446
[45] June 6, 1978

[54] HERBICIDAL 4-TRIFLUOROMETHYL-4-NITRODIPHENYL ETHERS

[75] Inventors: Horst O. Bayer, Levittown; Colin Swithenbank, Perkasie; Roy Y. Yih, Doylestown, all of Pa.

[73] Assignee: Rohm and Haas Company, Philadelphia, Pa.

[21] Appl. No.: 719,484

[22] Filed: Aug. 31, 1976

Related U.S. Application Data

[60] Continuation-in-part of Ser. No. 617,560, Sep. 29, 1975, and Ser. No. 617,562, Sep. 29, 1975, said Ser. No. 617,560, is a continuation-in-part of Ser. No. 331,719, Feb. 12, 1973, Pat. No. 3,928,416, said Ser. No. 617,562, is a division of Ser. No. 331,719, Feb. 12, 1973, Pat. No. 3,928,416, which is a continuation-in-part of Ser. No. 234,651, Mar. 14, 1972, Pat. No. 3,798,276.

[51] Int. Cl.² ............... A01N 9/20; C07C 79/46
[52] U.S. Cl. ............................. 71/109; 71/88; 71/92; 71/94; 71/103; 71/105; 71/108; 71/116; 71/118; 71/121; 71/123; 71/124; 260/293.75; 260/293.85; 260/348.45; 260/465 D; 260/465 E; 260/465 F; 260/520 C; 260/559 D; 260/570.7; 260/590 D; 260/607 AR; 260/609 F; 260/613 R; 544/163; 544/167; 544/395; 544/398; 560/21
[58] Field of Search ............. 260/471 R, 520 C; 71/108, 109, 116; 560/21

[56] References Cited

U.S. PATENT DOCUMENTS

| | | | |
|---|---|---|---|
| 3,546,229 | 12/1970 | Griot | 260/520 C X |
| 3,721,703 | 3/1973 | Nahm et al. | 260/471 R |
| 3,954,442 | 5/1976 | Becker et al. | 71/116 X |
| 3,979,437 | 9/1976 | Thiessen | 260/471 R |
| 4,047,929 | 9/1977 | Schmidt et al. | 71/116 X |
| 4,047,932 | 9/1977 | Albrecht et al. | 71/111 X |

*Primary Examiner*—Richard L. Raymond

[57] ABSTRACT

Compounds of the formula

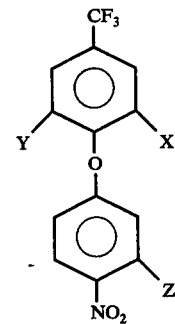

wherein
X is a hydrogen atom, a halogen atom, a trihalomethyl group, an alkyl group, or a cyano group,
Y is a hydrogen atom, a halogen atom, or a trihalomethyl group, and
Z is a substituted alkoxy group, and compositions containing these compounds exhibit herbicidal activity.

15 Claims, No Drawings

HERBICIDAL 4-TRIFLUOROMETHYL-4-NITRODIPHENYL ETHERS

CROSS REFERENCE TO RELATED APPLICATIONS

This application is a continuation-in-part of our co-pending applications Serial No. 617,560 and Serial No. 617,562, both filed September 29, 1975, which are in turn a continuation-in-part and a division, respectively, of Serial No. 331,719, filed February 12, 1973, now U.S. Patent 3,928,416, granted December 23, 1975, which is in turn a continuation-in-part of Serial No. 234,651, filed March 14, 1972, now U.S. Patent No. 3,798,276, granted March 19, 1974.

This invention relates to novel compounds which shown activity as herbicides, to novel herbicidal compositions which contain these compounds, and to new methods of controlling weeds with these herbicidal compositions.

Certain diphenyl ethers have been shown to be effective weed control agents. However, the herbicidal effectiveness of a given diphenyl ether cannot be predicted from an examination of the substituent groups attached to the phenyl rings in the ether, and often quite closely related compounds will have quite different weed control abilities. Various diphenyl ethers may have overlapping or complementary areas of activity or selectivity, and can thus be useful in combination to control a variety of weeds upon application of a single composition. Furthermore, the diphenyl ethers heretofore disclosed as herbicides are not completely effective. An ideal herbicide should give selective weed control, over the full growing season, with a single administration at low rates of application. It should be able to control all common weeds by killing them as the seed, the germinating seed, the seedling, and the growing plant. At the same time, the herbicide should be not phytotoxic to the crops to which it is applied and should decompose or otherwise be dissipated so as not to poison the soil permanently. The known diphenyl ether herbicides fall short of these ideals, and it would thus be desirable to have new herbicides which show even more selective control of undesirable plants among desirable crop plants or which complement the known diphenyl ethers in activity.

In accordance with the present invention, there is provided a new class of novel diphenyl ethers having the formula

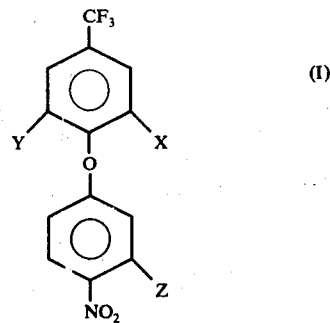

wherein
X is a hydrogen atom, a halogen atom, preferably a fluorine atom or a chlorine atom, a trihalomethyl group, preferably a trifluoromethyl group, a ($C_1$–$C_4$)alkyl group, preferably a methyl group, or a cyano group, Y is a hydrogen atom, a halogen atom, preferably a fluorine atom or a chlorine atom, or a trihalomethyl group, preferably a trifluoromethyl group, and Z is a hydroxy group, an alkoxy group, preferably having 1 to 6 carbon atoms, and most preferably 1 to 4 carbon atoms, an alkyl group, preferably having 1 to 4 carbon atoms, a halogen atom, preferably a chlorine atom or a fluorine atom, an amino group, preferably having up to 6 carbon atoms, an alkylthio group, preferably having 1 to 4 carbon atoms, a cyano group, a carboxy group, a carbalkoxy group, —$CO_2R$, preferably having 1 to 4 carbon atoms in the alkoxy moiety, a carboxyalkyl group, —$R'CO_2H$, preferably having up to 4 carbon atoms, a carbalkoxyalkyl group, —$R'CO_2R$, preferably having up to 6 carbon atoms, an alkanoyloxy group, —OCOR, preferably having up to 4 carbon atoms, optionally substituted with a halogen atom, or a carbamoyloxy group, —$OCONH_2$, —OCONHR, or —$OCONR_2$, preferably having up to 6 carbon atoms.

In the above definitions of the Z substitutent, R represents an alkyl group, and R' represents a divalent alkylene group. The alkyl or alkylene portion of the alkyl-containing X and X substituents can have either a straight- or branched-chain or a cyclic spatial configuration.

As used in the present specification and claims, the term "alkoxy group" is intended to include both unsubstituted alkoxy groups as well as alkoxy groups which have one or more of the hydrogen atoms, preferably one or two, most preferably one, replaced by a substituent group. Among the substituted alkoxy groups which Z can represent are alkoxy groups of preferably up to 4 carbon atoms substituted with a halogen atom, a hydroxy group, an alkoxy group, preferably having up to 4 carbon atoms, a carboxy group, or salts thereof, a carbalkoxy group, preferably having up to 4 carbon atoms in the ester alkoxy group, a trihaloalkyl group, preferably a trifluoromethyl group, an alkenyl group, preferably having 2 to 4 carbon atoms, an alkynyl group, preferably having 2 to 4 carbon atoms, most preferably an ethynyl group, an amino group, an alkyl or dialkylamino group, including heterocyclic substituents such as morpholino, piperazino, piperidino, and the like, and preferably having a total of up to 4 carbon atoms, an alkylthio group, preferably having up to 4 carbon atoms, a alkylsulfonyl group, preferably having up to 4 carbon atoms, an epoxy group, an alkylcarbonyl group, including halo-substituted alkylcarbonyl, and preferably having up to 4 carbon atoms in the alkyl group, most preferably methylcarbonyl, a carbamoyl group, including alkyl- or dialkyl-carbamoyl, preferably having a total of up to 4 carbon atoms in the alkyl substituents. In a preferred class of substituted alkoxy groups, the alkoxy group has the formula

wherein $Z^1$ is one of the substituents set forth above, $Z^2$ is a hydrogen atom or ($C_1$–$C_3$) alkyl group, and $n$ is 0 or 1. The most preferred subclass is that in which $Z^2$ is a methyl group and $n$ is 0. Other noteworthy subclasses include that in which $Z^2$ is a hydrogen atom and $n$ is 1 and that in which $Z^2$ is a methyl group and $n$ is 1.

The term "amino group" as used in the present specification and claims is intended to include an unsubstituted amino group, —$NH_2$, as well as amine groups having one or both hydrogen atoms replaced by substituent groups. Among the substituted amino groups which Z can represent are amino groups substituted with one or two alkyl groups, preferably having a total of up to 6 carbon atoms, halo-, hydroxy-, or alkoxy-substituted alkyl groups, preferably having a total of up to 6 carbon atoms, one or two alkylthio carbonyl groups, preferably having a total of up to 4 carbon atoms in the alkyl moiety, carboxy groups, carbalkoxy groups, preferably having up to 4 carbon atoms in the alkoxy group, carbamoyl groups, including alkyl or dialkylcarbamoyl groups, preferably having up to 4 carbon atoms in the alkyl moiety, alkylcarbonyl groups, preferably having up to 4 carbon atoms, or halo-substituted alkylcarbonyl groups, preferably having up to 4 carbon atoms. The substituted amino groups can also be heterocyclic amino groups, such as piperidino, piperazino, morpholino, pyrrolidinyl, and the like.

When the Z substituent is or contains a carboxy group, either the free acid or the salt form can be used. Typical salts are the agronomically-acceptable metal salts or ammonium salts. Among the metal salts are those in which the metal cation is an alkali metal cation, such as sodium, potassium, lithium, or the like, an alkaline earth metal cation, such as calcium, magnesium, barium, strontium, or the like, or a heavy metal cation, such as zinc, manganese cupric, cuprious, ferric, ferrous, titanium, aluminum or the like. Among the ammonium salts are those in which the ammonium cation has the formula $NR^1R^2R^3R^4$, wherein each of $R^1$, $R^2$, $R^3$, and $R^4$ is individually a hydrogen atom, a hydroxy group, a ($C_1$–$C_4$)alkoxy group, a ($C_1$–$C_{20}$)alkyl group, a ($C_3$–$C_8$)alkenyl group, a ($C_3$–$C_8$)alkynyl group, a ($C_2$–$C_8$), hydroxyalkyl group, a ($C_2$–$C_8$)alkoxyalkyl group, a ($C_2$–$C_6$)-aminoalkyl group, a ($C_2$–$C_6$)haloalkyl group, an amino group, a ($C_1$–$C_4$)alkyl- or di($C_1$–$C_4$)alkylamino group, a substituted or unsubstituted phenyl group, a substituted or unsubstituted phenyl group, a substituted or unsubstituted phenylalkyl group, having up to 4 carbon atoms in the alkyl moiety, or any two of $R^1$, $R^2$, $R^3$, or $R^4$ can be taken together to form with the nitrogen atom a 5- or 6-memeber heterocyclic ring, optionally having up to one additional hetero oxygen, nitrogen, or sulfur atom in the ring, and preferably saturated, such as a piperidine, morpholino, pyrrolidino, or piperazino ring, or the like, or any three of $R^1$, $R^2$, $R^3$, or $R^4$ can be taken together to form with the nitrogen atom a 5- or 6-member aromatic heterocyclic ring, such as a piperazole or pyridine ring. When the ammonium group contains a substituted phenyl or substituted phenylalkyl group, the substituents will generally be selected from halogen atoms, ($C_1$–$C_8$)alkyl groups, ($C_1$–$C_4$)alkoxy groups, hydroxy groups, nitro groups, trifluoromethyl groups, cyano groups, amino groups, ($C_1$–$C_4$)alkylthio groups, and the like. Such substituted phenyl groups preferably have up to two such substituents. Representative ammonium cations include ammonium, dimethylammonium, 2-ethylhexylammonium, bis(2-hydroxyethyl)-ammonium, tris(2-hydroxyethyl)ammonium, dicyclohexylammonium, t-octylammonium, 2-hydroxyethylammonium, morpholinium, piperidinium, 2-phenethylammonium, 2-methylbenzylammonium, n-hexylammonium, triethylammonium, trimethylammonium, tri(n-butyl)-ammonium, methoxyethylammonium, diisopropylammonium, pyridinium, diallylammonium, pyrazolium, propargylammonium, dimethylhydrazinium, hydroxyammonium, methoxyammonium, dodecylammonium, octadecylammonium, 4-dichlorophenylammonium, 4-nitrobenzylammonium, benzyltrimethylammonium, 2-hydroxyethyldimethyloctadecylammonium, 2-hydroxyethyldiethyloctylammonium, decyltrimethylammonium, hexyltriethylammonium, 4-methylbenzyltrimethylammonium, and the like.

When Z is an alkyl group, it may be optionally substituted with a hydroxy group, a ($C_1$–$C_4$)alkoxy group, or a halogen atom, preferably a chlorine atom.

These novel compounds have been found to show unexpected activity as weed control agents. In a preferred embodiment of the invention, X is a halogen atom or a cyano group, Y is a hydrogen atom or a halogen atom, and Z is an alkoxy group.

Examples of the compounds of the invention embraced by Formula I include:

2-chloro-$\alpha,\alpha,\alpha$-trifluoro-p-tolyl-4-nitro-m-tolyl ether, 2-bromo-$\alpha,\alpha,\alpha$-trifluoro-p-tolyl-3-butyl-4-nitrophenyl ether, 2,$\alpha,\alpha,\alpha$-tetrafluoro-p-tolyl-4-nitro-3-n-propoxyphenyl ether, 2-chloro-6,$\alpha,\alpha,\alpha$-tetrafluoro-p-tolyl-3-methylthio-4-nitrophenyl ether, 2-chloro-$\alpha,\alpha,\alpha$-trifluoro-p-tolyl-3-propyl-4-nitrophenyl ether, 2-chloro-$\alpha,\alpha,\alpha$-trifluoro-p-tolyl-3-ethoxy-4-nitrodiphenyl ether, $\alpha,\alpha,\alpha$-trifluoro-2-iodo-p-tolyl-3-ethoxy-4-nitrophenyl ether, 2,6-dichloro-$\alpha,\alpha,\alpha$-trifluoro-p-tolyl-4-nitro-3-n-propoxyphenyl ether, $\alpha,\alpha,\alpha,\alpha',\alpha',\alpha'$-hexafluoro-2,4-xylyl-3-n-butoxy-4-nitrophenyl ether, 2-cyano-$\alpha,\alpha,\alpha$-trifluoro-p-tolyl-3-ethoxy-4-nitrophenyl ether, 2-chloro-6-cyano-$\alpha,\alpha,\alpha$-trifluoro-p-tolyl-4-nitro-3-n-propoxyphenyl ether, 2-cyano-$\alpha,\alpha,\alpha$-trifluoro-p-tolyl-3-carboxy-4-nitrophenyl ether, 2,6-dibromo-$\alpha,\alpha,\alpha$-trifluoro-p-tolyl-3-methoxymethoxy-4-nitrophenyl ether, 2-chloro-$\alpha,\alpha,\alpha$-trifluoro-p-tolyl-3-(2-hydroxyethoxy)-4-nitrophenyl ether, 2,$\alpha,\alpha,\alpha$-tetrafluoro-p-tolyl-4-nitro-3-n-propylaminophenyl ether, 2-chloro-$\alpha,\alpha,\alpha$-trifluoro-p-tolyl-3-dimethylamino-4-nitrophenyl ether, 2-cyano-$\alpha,\alpha,\alpha$-trifluoro-p-tolyl-3-carbethoxy-4-nitrophenyl ether 2,6-dichloro-$\alpha,\alpha,\alpha$-trifluoro-p-tolyl-3-carbethoxy-4-nitrophenyl ether 2-ethyl-$\alpha,\alpha,\alpha$-trifluoro-p-tolyl-3-(2-carboxy ethoxy)-4-nitrophenyl ether $\alpha,\alpha,\alpha,\alpha',\alpha',\alpha'$-hexafluoro-2,4-xylyl-3-carbethoxymethyl-4-nitrophenyl ether, 2-cyano-$\alpha,\alpha,\alpha$-trifluoro-p-tolyl-3-(2-carboxy propyl)-4-nitrophenyl ether, 2,$\alpha,\alpha,\alpha$-tetrafluoro-p-tolyl-3-carbethoxymethoxy-4-nitrophenyl ether, 2-chloro-$\alpha,\alpha,\alpha$-trifluoro-p-tolyl-3-(3,3-diethylureido)-4-nitrophenyl ether, 2-chloro-6-cyano-$\alpha,\alpha,\alpha$-trifluoro-p-tolyl-3-acetamido-4-nitrophenyl ether, 2-chloro-$\alpha,\alpha,\alpha$-trifluoro-p-tolyl-3-carbethoxyamino-4-nitrophenyl ether, 2-chloro-$\alpha,\alpha,\alpha$-trifluoro-p-tolyl-3-chloro-4-nitrophenyl ether, 2-chloro-$\alpha,\alpha,\alpha$-trifluoro-p-tolyl-3-hydroxy-4-nitrophenyl ether, 2-bromo-$\alpha,\alpha,\alpha$-trifluoro-p-tolyl-3-butynyloxy-4-nitrophenyl ether 2-cyano-$\alpha,\alpha,\alpha$-trifluoro-p-tolyl-3-(2-methyl)-propynyloxy-4-nitrophenyl ether, 2,6-dichloro-α,α,α-trifluoro-p-tolyl-3-(2,2,2-trifluoro)-ethoxy-4-nitrophenyl ether,
2-chloro-α,α,α-trifluoro-p-tolyl-3-(2-dimethylaminoethoxy)-4-nitrophenyl ether,
2-bromo-α,α,α-trifluoro-p-tolyl-3-acetoxy-4-nitrophenyl ether,
α,α,α,α',α',α'-hexafluoro-2,4-xylyl-3-(2-hydroxyethylamino)-4-nitrophenyl ether
α$^4$,α$^4$,α$^4$-trifluoro-2,4-xylyl-3-amino-4-nitrophenyl ether,
2-chloro-α,α,α-trifluoro-p-tolyl-3-morpholino-4-nitrophenyl ether,
2-cyano-α,α,α-trifluoro-p-tolyl-3-(N-methylcarbamoyloxy)-4-nitrophenyl ether,
2-chloro-6,α,α,α-tetrafluoro-p-tolyl-3-propionamido-4-nitrophenyl ether,
2-chloro-α,α,α-trifluoro-p-tolyl-3-chloroacetamido-4-nitrophenyl ether,
α$^4$,α$^4$,α$^4$-trifluoro-2,4-xylyl-3-(2,3-epoxypropoxy)-4-nitrophenyl ether,
2-chloro-α,α,α-trifluoro-p-tolyl-3-(2,3-dihydroxypropoxy)-4-nitrophenyl ether,
2-cyano-α,α,α-trifluoro-p-tolyl-3-(2-methylthioethoxy)-4-nitrophenyl ether,
2-chloro-α,α,α-trifluoro-p-tolyl-3-(1-ethyl-3-methylureido)-4-nitrophenyl ether,
2-bromo-α,α,α-trifluoro-p-tolyl-3-(2-methylsulfonylethoxy)-4-nitrophenyl ether,
α,α,α,α',α',α'-hexafluoro-2,4-xylyl-3-(3-methylureido)-4-nitrophenyl ether,
2-cyano-α,α,α-trifluoro-p-tolyl-3-ethylthiocarbonylamino-4-nitrophenyl ether,
2-cyano-α,α,α-trifluoro-p-tolyl-3-cyano-4-nitrophenyl ether,
2,6-dichloro-α,α,α-trifluoro-p-tolyl-3-carboxy-4-nitrophenyl ether,
2-chloro-α,α,α-trifluoro-p-tolyl-3-(1-carbamoylethoxy)-4-nitrophenyl ether,
2-bromo-α,α,α-trifluoro-p-tolyl-3-(3-oxobutoxy)-4-nitrophenyl ether,
and the like.

The novel diphenyl ethers of the invention are useful both as preemergence and as postemergence herbicides. Preemergence herbicides are ordinarily used to treat the soil in which the desired crop is to be planted by application either before seeding, during seeding, or as in most applications, after seeding and before the crop emerges. Postemergence herbicides are those which are applied after the plants have emerged and during their growth period.

Among the crops on which the diphenyl ethers of the invention can be advantageously employed are, for example, cotton, soybeans, peanuts, safflower, beans, peas, carrots, corn, wheat, and other cereal crops.

Diphenyl ethers of the invention are useful for controlling weeds in rice crops. When used in transplanted rice crops, the ethers can be applied either preemergence or postemergence to the weeds—that is, they can be applied to the growth medium of the transplanted plants either before the weed plants have emerged or while they are in their early stages of growth. The ethers can be applied to the growth medium either before or after the rice has been transplanted to that medium.

The diphenyl ethers of the invention can be applied in any amount which will give the required control of weeds. A preferred rate of application of the herbicides of the invention is from about 0.1 to about 12, and most preferably about 0.25 to 4, pounds of the diphenyl ether per acre.

Under some conditions, the diphenyl ethers of the invention may be advantageously incorporated into the soil or other growth medium prior to planting a crop. This incorporation can be carried out by any convenient means, including by simple mixing with the soil, by applying the diphenyl ether to the surface of the soil and then disking or dragging into the soil to the desired depth, or by employing a liquid carrier to accomplish the necessary penetration and impregnation.

A diphenyl ether of the invention can be applied to the growth medium or to plants to be treated either by itself or, as is generally done, as a component in a herbicidal composition or formulation which also comprises an agronomically acceptable carrier. By agronomically acceptable carrier is meant any substance which can be used to dissolve, disperse, or diffuse a herbicidal compound in the composition without impairing the effectiveness of the herbicidal compound and which by itself has no detrimental effect on the soil, equipment, crops, or agronomic environment. Mixtures of the diphenyl ethers of the invention may also be used in any of these herbicidal formulations. The herbicidal compositions of the invention can be either solid or liquid formulations or solutions. For example, the diphenyl ethers can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in postemergence applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers Annual".

The diphenyl ether compounds of this invention can be dissolved in any appropriate solvent. Examples of solvents which are useful in the practice of this invention include alcohols, ketones, aromatic hydrocarbons, halogenated hydrocarbons, dimethylformamide, dioxane, dimethyl sulfoxide, and the like. Mixtures of these solvents can also be used. The concentration of the solution can vary from about 2% to about 98% with a preferred range being about 25% to about 75%.

For the preparation of emulsifiable concentrates, the diphenyl ether can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersion in water. Suitable emulsifiers include, for example, the ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or a water-soluble salt of a polyacrylic acid. The concentration of the active ingredient in emulsifiable concentrates is usually about 10% to 60% and in flowable emulsion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of about 20% to 98%, preferably about 40% to 75%. A dispersing agent can constitute about 0.5% to about 3% of the composition, and a wetting agent can constitute from about 0.1% to about 5% of the composition.

Dusts can be prepared by mixing the compounds of the invention with finely divided inert solids which may be organic or inorganic in nature. Materials useful for this purpose include, for example, botanical flours, silicas, silicates, carbonates and clays. One convenient method of preparing a dust is to dilute a wettable powder with a finely divided carrier. Dust concentrates containing about 20% to 80% of the active ingredient are commonly made and are subsequently diluted to about 1% to 10% use concentration.

Granular formulations can be prepared by impregnating a solid such as granular fuller's earch, vermiculite, ground corn cobs, seed hulls, including bran or other grain-hulls, or similar material. A solution of one or more of the diphenyl ethers in a volatile organic solvent can be sprayed or mixed with the granular solid and the solvent then removed by evaporation. The granular material can have any suitable size, with a preferable size range of 16 to 60 mesh. The diphenyl ether will usually comprise about 2 to 15% of the granular formulation.

The diphenyl ethers of the invention can also be mixed with fertilizers or fertilizing materials before their application. In one type of solid fertilizing composition in which the diphenyl ethers can be used, particles of a fertilizer or fertilizing ingredients, such as ammonium sulfate, ammonium nitrate, or ammonium phosphate, can be coated with one or more of the ethers. The solid diphenyl ethers and solid fertilizing material can also be admixed in mixing or blending equipment, or they can be incorporated with fertilizers in granular formulations. Any relative proportion of diphenyl ether and fertilizer can be used which is suitable for the crops and weeds to be treated. The diphenyl ether will commonly be from about 5% to about 25% of the fertilizing composition. These compositions provide fertilizing materials which promote the rapid growth of desired plants, and at the same time control the growth of undesired plants.

The diphenyl ethers of the invention can be applied as herbicidal sprays by methods commonly employed, such as conventional high-gallonage hydraulic sprays, low gallonage sprays, airblast spray, aerial sprays and dusts. For low volume applications a solution of the compound is usually used. The dilution and rate of application will usually depend upon such factors as the type of equipment employed, the method of application, the area to be treated and the type and stage of development of the weeds.

For some applications, it may be desirable to add one or more other herbicides along with diphenyl ethers of the invention. Examples of other herbicides which can be incorporated to provide additional advantages and effectiveness include:

Carboxylic Acids and Derivatives 2,3,6-trichlorobenzoic acid and its salts
2,3,5,6-tetrachlorobenzoic acid and its salts
2-methoxy-3,5,6-trichlorobenzoic acid and its salts
2-methoxy-3,6-dichlorobenzoic acid and its salts
2-methyl-3,6-dichlorobenzoic acid and its salts
2,3-dichloro-6-methylbenzoic acid and its salts
2,4-dichlorophenoxyacetic acid and its salts and esters
2,4,5-trichlorophenoxyacetic acid and its salts and esters
2-methyl-4-chlorophenoxyacetic acid and its salts and esters
2-(2,4,5-trichlorophenoxy)propionic acid and its salts and esters
4-(2,4-dichlorophenoxy)butyric acid and its salts and esters
4-(2-methyl-4-chlorophenoxy)butyric acid and its salts and esters
2,3,6-trichlorophenylacetic acid and its salts
3,6-endoxohexahydrophthalic acid
dimethyl 2,3,5,6-tetrachloroterephthalate
trichloroacetic acid and its salts
2,2-dichloropropionic acid and its salts
2,3-dichloroisobutyric acid and its salts Carbamic Acid Derivatives ethyl N,N-di(n-propyl)thiolcarbamate
propyl N,N-di(n-propyl)thiolcarbamate
ethyl N-ethyl-N-(n-butyl)thiolcarbamate
propyl N-ethyl-N-(n-butyl)thiolcarbamate
2-chloroallyl N,N-diethyldithiocarbamate
N-methyldithiocarbamic acid salts
ethyl 1-hexamethyleneiminecarbothiolate
isopropyl N-phenylcarbamate
isopropyl N-(m-chlorophenyl)carbamate
4-chloro-2-butynyl N-(m-chlorophenyl)carbamate
methyl N-(3,4-dichlorophenyl)carbamate Phenols dinitro-o-(sec-butyl)phenol and its salts
pentachlorophenol and its salts Substituted Ureas 3-(3,4-dichlorophenyl)-1,1-dimethylurea
3-phenyl-1,1-dimethylurea
3-(3,4-dichlorophenyl)-3-methoxy-1,1-dimethylurea
3-(4-chlorophenyl)-3-methoxy-1,1-dimethylurea
3-(3,4-dichlorophenyl)-1-n-butyl-1-methylurea
3-(3,4-dichlorophenyl)-1-methoxy-1-methylurea
3-(4-chlorophenyl)-1-methoxy-1-methylurea
3-(3,4-dichlorophenyl)-1,1,3-trimethylurea
3-(3,4-dichlorophenyl)-1,1-diethylurea
dichloral urea Substituted Triazines 2-chloro-4,6-bis(ethylamino)-s-triazine
2-chloro-4-ethylamino-6-isopropylamino-s-triazine
2-chloro-4,6-bis(methoxypropylamino)-s-triazine
2-methoxy-4,6-bis(isopropylamino)-s-triazine
2-chloro-4-ethylamino-6-(3-methoxypropylamino)-s-triazine
2-methylmercapto-4,6-bis(isopropylamino)-s-triazine
2-methylmercapto-4,6-bis(ethylamino)-s-triazine
2-methylmercapto-4-ethylamino-6-isopropylamino-s-triazine
2-chloro-4,6-bis(isopropylamino)-s-triazine
2-methoxy-4,6-bis(ethylamino)-s-triazine
2-methoxy-4-ethylamino-6-isopropylamino-s-triazine 2-methylmercapto-4-(2-methoxyethylamino)-6-isopropylamino-s-triazine Diphenyl Ether Derivatives 2,4-dichloro-4'-nitrodiphenyl ether
2,4,6-trichloro-4'-nitrodiphenyl ether
2,4-dichloro-6-fluoro-4'-nitrodiphenyl ether
3-methyl-4'-nitrodiphenyl ether
3,5-dimethyl-4'-nitrodiphenyl ether
2,4'-dinitro-4-trifluoromethyldiphenyl ether
2,4-dichloro-3'-methoxy-4'-nitrodiphenyl ether Anilides N-(3,4-dichlorophenyl)propionamide
N-(3,4-dichlorophenyl)methacrylamide
N-(3-chloro-4-methylphenyl)-2-methylpentanamide
N-(3,4-dichlorophenyl)trimethylacetamide
N-(3,4-dichlorophenyl)-α,α-dimethylvaleramide
N-isopropyl-N-phenylchloroacetamide
N-n-butoxymethyl-N-(2,6-diethylphenyl)chloroacetamide
N-n-methoxymethyl-N-(2,6-diethylphenyl)chloroacetamide Uracils 5-bromo-3-s-butyl-6-methyluracil
5-bromo-3-cyclohexyl-1,6-dimethyluracil
3-cyclohexyl-5,6-trimethyleneuracil
5-bromo-3-isopropyl-6-methyluracil
3-tert-butyl-5-chloro-6-methyluracil Nitriles 2,6-dichlorobenzonitrile
diphenylacetonitrile
3,5-dibromo-4-hydroxybenzonitrile
3,5-diiodo-4-hydroxybenzonitrile Other Organic Herbicides 2-chloro-N,N-diallylacetamide
N-(1,1-dimethyl-2-propynyl)-3,5-dichlorobenzamide
maleic hydrazide
3-amino-1,2,4-triazole
monosodium methanearsonate
disodium methanearsonate
N,N-dimethyl-α,α-diphenylacetamide
N,N-di(n-propyl)-2,6-dinitro-4-trifluoromethylaniline
N,N-di(n-propyl)-2,6-dinitro-4-methylaniline
N,N-di(n-propyl)-2,6-dinitro-4-methylsulfonylaniline
O-(2,4-dichlorophenyl)-O-methyl-isopropylphosphoramidothioate
4-amino-3,5,6-trichloropicolinic acid
2,3-dichloro-1,4-naphthoquinone
di(methoxythiocarbonyl)disulfide
3-isopropyl-1H-2,1,3-benzothiadiazin-(4)3H-one-2,2-dioxide
6,7-dihydrodipyridol[1,2-a:2',1'-c]pyrazidinium salts
1,1'-dimethyl-4,4'-bipyridinium salts
3,4,5,6-tetrahydro-3,5-dimethyl-2-thio-2H-1,3,5-thiadiazine.

When mixtures of herbicides are employed, the relative proportions which are used will depend upon the crop to be treated and the degree of selectivity in weed control which is desired.

The diphenyl ethers of the invention or their precursors can be prepared by reacting a suitably substituted phenol, or the potassium or sodium salt of the phenol, with a suitably substituted halobenzene, such as a chloro- or fluorobenzene in the presence of an alkaline agent. In addition, the substituted alkoxy diphenyl ethers or their precursors can be prepared by reacting the corresponding diphenyl ether precursor in which Z in Formula I is a good leaving group, such as a halogen atom, preferably a chlorine atom, a substituted phenoxy group, such as a 2-chloro-4-trifluoromethylphenoxy group, or the like, with an appropriate substituted carbinol, such as a carbinol of the formula

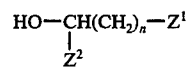

wherein $Z^1$, $Z^2$, and $n$ are as defined above. This reaction is generally carried out at a temperature of about 0° to about 200° C. The reaction can be carried out in any inert, preferably nonpolar, solvent in which the reactants are at least partially soluble, including benzene, dioxane, and the like, and usually in the presence of a base such as potassium hydroxide, potassium carbonate, or the like.

Diphenyl ethers prepared by the above techniques can also be used as precursors in preparing compounds of the invention. For example, the compounds of the invention in which Z is hydroxy may be converted to the α-oxymethylene carboxylic esters by condensation with α-halo esters in the presence of bases such as potassium carbonate or hydroxide to give compounds in which $Z^1$ is carbalkoxy. These esters in turn may be converted by conventional techniques to the corresponding carboxylic acids, acid chlorides and amides. Other typical postreactions include the oxidation, for example using peracid, of 2-methylthioethoxy to 2-methylsulfonylethoxy and the hydration, for example using mercuric ion, of (1-ethynyl)ethoxy to 1-acetylethoxy, and the like. In addition, compounds of the invention can be made by nitration of suitable precursors without a nitro group prepared by the above techniques.

The salts of the invention can be prepared by any convenient art-recognized method, such as by reacting a metal hydroxide, a metal hydride, or an amine or ammonium salt, such as a halide, hydroxide, or alkoxide, with the free acid, or reacting a quaternary ammonium salt, such as a chloride, a bromide, nitrate, or the like with a metal salt of the invention in a suitable solvent. When metal hydroxides are used as reagents, useful solvents include water, glyme, dioxane, tetrahydrofuran, methanol, ethanol, isopropanol and the like. When metal hydrides are used as reagents, useful solvents include nonhydroxylic solvents such as dioxane, glyme, tetrahydrofuran, diethyl ether, hydrocarbon, including toluene, benzene, xylene, hexane, pentane, heptane, and octane, dimethylformamide, and the like. When amines are used as reagents, useful solvents include alcohols, such as methanol or ethanol, hydrocarbons, such as benzene, toluene, xylene, hexane, and the like, tetrahydrofuran, glyme, dioxane, or water. When ammonium salts are used as reagents, useful solvents include water, alcohols, such as methanol or ethanol, glyme, tetrahydrofuran, or the like. When the ammonium salt is other than a hydroxide or alkoxide, an additional base, such as a potassium or sodium hydroxide, hydride, or alkoxide is generally used. The particular choice of solvent will depend on the relative solubilities of the starting materials and the resultant salts, and slurries rather than solutions, of certain reagents may be used to obtain the salts. Generally, equivalent amounts of the starting reagents are used and the salt-forming reaction is carried out at about 0° to about 100° C., and preferably at about room temperature.

The following examples will further illustrate this invention but are not intended to limit it in any way. In Table I, typical diphenyl ethers of the invention are listed, with their melting points and elemental analyses. Specific, illustrative preparations of the compounds of Examples 3, 7, 10, 19, 21, 25, 26, 30, 32, 37, 47, 48, 49, 51, 55, 56, 58, 59, 60, and 61 are described after Table I.

TABLE I
Diphenyl Ethers - Physical Data

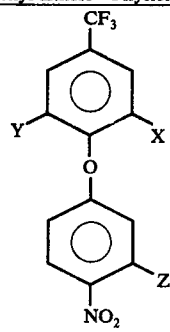

| Example No. | X | Y | Z | m.p. (° C) | | %C | %H | %N | %Cl | %F |
|---|---|---|---|---|---|---|---|---|---|---|
| 1 | H | H | OC$_2$H$_5$ | 72–75 | found | 54.67 | 3.75 | 4.19 | | 15.25 |
| | | | | | reqs. | 55.05 | 3.70 | 4.28 | | 17.42 |
| 2 | Cl | H | OCH$_3$ | 95–100 | found | 48.78 | 2.89 | 4.01 | 9.65 | 14.91 |
| | | | | | reqs. | 48.33 | 2.61 | 4.03 | 10.20 | 16.40 |
| 3 | Cl | H | OC$_2$H$_5$ | 83–84 | found | 49.85 | 3.33 | 3.68 | 9.90 | 15.51 |
| | | | | | reqs. | 49.80 | 3.07 | 3.87 | 9.80 | 15.75 |
| 4 | Cl | H | OC$_3$H$_7$-i | 49.5–51 | found | 51.02 | 3.58 | 3.52 | 9.62 | 15.58 |
| | | | | | reqs. | 51.18 | 3.49 | 3.73 | 9.42 | 15.16 |
| 5 | Cl | H | OC$_3$H$_7$-n | 75–76 | found | 51.36 | 3.60 | 3.62 | 9.34 | 15.00 |
| | | | | | reqs. | 51.18 | 3.49 | 3.73 | 9.42 | 15.16 |
| 6 | Cl | H | OC$_4$H$_9$-n | 51–52 | found | 52.07 | 4.03 | 3.38 | 9.28 | 14.65 |
| | | | | | reqs. | 52.42 | 3.88 | 3.59 | 9.10 | 14.63 |
| 7 | CN | H | OC$_2$H$_5$ | 143–145 | found | 54.84 | 3.36 | 8.01 | | 15.85 |
| | | | | | reqs. | 52.18 | 3.01 | 7.61 | | 15.48 |
| 8 | CN | H | OC$_3$H$_7$-n | 96.5–98 | found | 55.70 | 3.65 | 7.56 | | |
| | | | | | reqs. | 55.74 | 3.58 | 7.65 | | 15.56 |
| 9 | CN | H | CH$_3$ | 86–88.5 | found | 55.95 | 2.80 | 8.62 | | 17.68 |
| | | | | | reqs. | 55.90 | 2.81 | 8.72 | | 17.69 |
| 10 | Cl | H | OH | 68–70 | found | 47.07 | 2.11 | 4.00 | 10.76 | 17.00 |
| | | | | | reqs. | 46.79 | 2.12 | 4.20 | 10.63 | 17.08 |
| 11 | Cl | H | OCH$_2$CF$_3$ | 78–80 | found | 43.30 | 1.77 | 3.22 | 8.60 | 27.60 |
| | | | | | reqs. | 43.35 | 1.94 | 3.37 | 8.54 | 27.40 |
| 12 | Cl | H | OCH$_2$CH=CH$_2$ | 76.78.5 | found | 51.76 | 2.77 | 3.75 | 9.51 | 15.32 |
| | | | | | reqs. | 5.42 | 2.97 | 3.75 | 9.48 | 15.25 |
| 13 | Cl | H | OCH$_2$C≡CH | 89–93 | found | 51.83 | 2.22 | 3.52 | 9.61 | 15.31 |
| | | | | | reqs. | 51.70 | 2.44 | 3.77 | 9.54 | 15.33 |
| 14 | Cl | H | OCH$_2$CH$_2$C≡CCH$_3$ | 93–94 | found | 53.99 | 2.95 | 3.35 | 8.93 | 14.12 |
| | | | | | reqs. | 54.10 | 3.28 | 3.50 | 8.87 | 14.25 |
| 15 | Cl | H | OCH$_2$CH$_2$OH | 76–77 | found | 47.53 | 2.92 | 3.55 | 9.88 | 14.98 |
| | | | | | reqs. | 47.70 | 2.94 | 3.71 | 9.38 | 15.09 |
| 16 | Cl | H | OCH$_2$CH$_2$OC$_2$H$_5$ | 62–64 | found | 50.75 | 3.82 | 3.37 | 8.48 | 14.00 |
| | | | | | reqs. | 50.32 | 3.73 | 3.45 | 8.74 | 14.05 |
| 17 | Cl | H | OCH$_2$CH$_2$N(CH$_3$)$_2$ | oil | found | 50.30 | 3.76 | 6.42 | 9.19 | 13.80 |
| | | | | | reqs. | 50.44 | 3.98 | 6.92 | 8.76 | 14.03 |
| 18 | Cl | H | OCOCH$_3$ | 85–89 | found | 47.82 | 2.50 | 3.65 | 9.58 | 14.79 |
| | | | | | reqs. | 47.90 | 2.42 | 3.73 | 9.44 | 15.20 |
| 19 | Cl | H | NHC$_2$H$_5$ | 82–83 | found | 50.01 | 3.23 | 7.82 | 9.95 | 15.48 |
| | | | | | reqs. | 49.94 | 3.35 | 7.77 | 9.83 | 15.80 |
| 20 | Cl | H | N(CH$_3$)$_2$ | 82–83 | found | 50.27 | 3.46 | 7.95 | 9.62 | 15.50 |
| | | | | | reqs. | 49.97 | 3.35 | 7.77 | 9.83 | 15.80 |
| 21 | Cl | H | N(C$_2$H$_5$)$_2$ | *170° C/0.01mm | found | 52.80 | 3.89 | 7.10 | 9.25 | 14.58 |
| | | | | | reqs. | 52.50 | 4.15 | 7.20 | 9.12 | 14.68 |
| 22 | Cl | H | NHCH$_2$CH$_2$OH | 85–87 | found | 46.22 | 3.33 | 7.06 | 8.50 | 15.30 |
| | | | | | reqs. | 47.82 | 3.21 | 7.44 | 9.42 | 15.13 |
| 23 | Cl | H | OCH$_2$CO$_2$H | 94–96 | found | 45.96 | 2.21 | 3.71 | 9.17 | 13.99 |
| | | | | | reqs. | 46.00 | 2.32 | 3.57 | 9.05 | 14.56 |
| 24 | Cl | H | OCH$_2$CO$_2$C$_2$H$_5$ | 76–77 | found | 48.49 | 2.93 | 3.25 | 8.58 | 13.65 |
| | | | | | reqs. | 48.60 | 3.13 | 3.34 | 8.46 | 13.62 |
| 25 | Cl | H | OCH(CH$_3$)CO$_2$H | 108–109 | found | 47.34 | 2.63 | 3.52 | 8.78 | 13.70 |
| | | | | | reqs. | 47.35 | 2.73 | 3.45 | 8.73 | 14.05 |
| 26 | Cl | H | OCH(CH$_3$)CO$_2$C$_2$H$_5$ | 71–72.5 | found | 49.78 | 3.40 | 3.07 | 8.31 | 12.90 |
| | | | | | reqs. | 49.85 | 3.49 | 3.23 | 8.18 | 13.15 |
| 27 | Cl | H | NH$_2$ | 85.5–89.5 | found | 48.6 | 2.87 | 8.01 | 10.37 | 17.09 |
| | | | | | reqs. | 46.93 | 2.42 | 8.42 | 10.66 | 17.14 |
| 28 | Cl | H | N⌒O (morpholino) | *180–185/0.04mm | found | 50.61 | 3.39 | 6.80 | 8.95 | 13.71 |
| | | | | | reqs. | 50.70 | 3.50 | 9.96 | 8.80 | 14.15 |
| 29 | Cl | H | OCH$_2$CH$_2$C≡CH | 104–105.5 | found | 52.67 | 3.05 | 3.44 | 9.41 | 14.33 |
| | | | | | reqs. | 53.00 | 2.87 | 3.63 | 9.20 | 14.80 |
| 30 | Cl | H | OCH(CH$_3$)C≡CH | 40–42 | found | 52.59 | 2.77 | 3.61 | 9.66 | 15.27 |
| | | | | | reqs. | 53.00 | 2.87 | 3.63 | 9.20 | 14.80 |
| 31 | Cl | H | OCH$_2$CH$_2$COCH$_3$ | 74–76 | found | 50.44 | 3.27 | 3.36 | 8.81 | 14.49 |
| | | | | | reqs. | 50.60 | 3.25 | 3.47 | 8.75 | 14.12 |

TABLE I-continued
Diphenyl Ethers - Physical Data

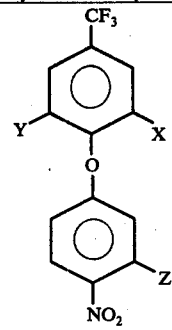

| | | | | | | Analysis | | | | |
|---|---|---|---|---|---|---|---|---|---|---|
| Example No. | X | Y | Z | m.p. (° C) | | %C | %H | %N | %Cl | %F |
| 32 | Cl | H | OCH(CH₃)COCH₃ | oil | found | 48.07 | 3.26 | 3.17 | 8.18 | 14.26 |
| | | | | | reqs. | 50.60 | 3.25 | 3.47 | 8.75 | 14.12 |
| 33 | Cl | H | OCONHCH₃ | 85–88 | found | 45.57 | 3.21 | 8.02 | 9.48 | 14.76 |
| | | | | | reqs. | 46.10 | 2.58 | 7.18 | 9.08 | 14.60 |
| 34 | Cl | H | NHCOC₂H₅ | oil | found | 49.50 | 3.14 | 7.01 | 9.12 | 14.71 |
| | | | | | reqs. | 49.40 | 3.12 | 7.20 | 9.12 | 14.68 |
| 35 | Cl | H | NHCOCH₂Cl | oil | found | 44.51 | 1.85 | 6.60 | 17.34 | 14.90 |
| | | | | | reqs. | 44.03 | 2.22 | 6.85 | 17.33 | 13.93 |
| 36 | Cl | H | CH₃ | *135° C/0.08mm | found | 50.91 | 2.81 | 4.31 | 10.63 | 16.95 |
| | | | | | reqs. | 50.70 | 2.73 | 4.22 | 10.69 | 17.19 |
| 37 | Cl | H | Cl | *153° C/0.24mm | found | 44.15 | 1.58 | 4.09 | 18.13 | 18.48 |
| | | | | | reqs. | 44.34 | 1.72 | 3.98 | 20.14 | 16.19 |
| 38 | Cl | H | OCH₂CHCH₂ (epoxide) | 49–53 | found | 47.88 | 2.50 | 3.32 | 10.58 | 14.82 |
| | | | | | reqs. | 49.30 | 2.84 | 3.60 | 9.11 | 14.63 |
| 39 | Cl | H | OCH₂CHOHCH₂OH | 59–64 | found | 47.49 | 3.32 | 3.35 | 8.88 | 14.73 |
| | | | | | reqs. | 49.00 | 3.35 | 3.58 | 9.05 | 14.58 |
| 40 | Cl | H | OCH₂CH₂SCH₃ | 42–45 | found | 47.09 | 2.95 | 3.34 | 8.80 | 14.05 |
| | | | | | reqs. | 47.12 | 3.21 | 3.44 | 8.69 | 13.98 |
| 41 | Cl | H | N(C₃H₇-n)₂ | oil | found | 54.04 | 4.62 | 6.34 | 8.71 | 13.55 |
| | | | | | reqs. | 54.75 | 4.84 | 6.72 | 8.50 | 13.67 |
| 42 | Cl | H | OCH₂CH₂SO₂CH₃ | 127.5–129.5 | found | 43.53 | 2.71 | 2.99 | 8.27 | 13.19 |
| | | | | | reqs. | 43.69 | 2.98 | 3.19 | 8.06 | 12.96 |
| 43 | Cl | H | N(CH₃)CH₂CH₂OH | oil | found | 48.95 | 3.65 | 7.18 | 9.29 | 14.87 |
| | | | | | reqs. | 49.18 | 3.61 | 7.17 | 9.07 | 14.59 |
| 44 | Cl | H | NHCONHCH₃ | 204–208 | found | 46.52 | 2.56 | 10.76 | 9.40 | 14.47 |
| | | | | | reqs. | 46.22 | 2.85 | 10.78 | 9.10 | 14.63 |
| 45 | Cl | H | NHCOSC₂H₅ | 111–112 | found | 45.76 | 2.88 | 6.77 | 8.58 | 13.24 |
| | | | | | reqs. | 45.66 | 2.88 | 6.66 | 8.42 | 13.55 |
| 46 | Cl | H | N(COSC₂H₅)₂ | 99–100 | found | 45.08 | 3.14 | 5.53 | 7.20 | 11.03 |
| | | | | | reqs. | 44.84 | 3.17 | 5.50 | 6.97 | 11.20 |
| 47 | Cl | H | CN | 95–103 | found | 49.92 | 1.82 | 7.68 | 11.57 | 15.69 |
| | | | | | reqs. | 49.05 | 1.77 | 8.18 | 10.35 | 16.65 |
| 48 | Cl | H | CO₂H | 140–150 | found | 46.26 | 1.86 | 3.45 | 14.48 | |
| | | | | | reqs. | 46.50 | 1.95 | 3.87 | 9.82 | 15.78 |
| 49 | Cl | H | CO₂CH₃ | oil | found | 47.77 | 2.64 | 3.48 | 10.49 | 12.93 |
| | | | | | reqs. | 47.90 | 2.42 | 3.73 | 9.45 | 15.20 |
| 50 | Cl | H | OCH(CH₃)CO₂CH₃ | 68–70 | found | 48.58 | 2.98 | 3.15 | 8.58 | 13.73 |
| | | | | | reqs. | 48.60 | 2.98 | 3.35 | 8.43 | 13.58 |
| 51 | Cl | H | OCH(CH₃)CONH₂ | 108–111 | found | 47.61 | 3.21 | 6.70 | 8.98 | 14.37 |
| | | | | | reqs. | 47.50 | 2.99 | 6.93 | 8.78 | 14.10 |
| 52 | Cl | H | OCH(CH₃)CONHCH₃ | 121–126 | found | 48.68 | 3.53 | 6.54 | 8.78 | 13.72 |
| | | | | | reqs. | 48.80 | 3.37 | 6.70 | 8.48 | 13.62 |
| 53 | Cl | H | OCH(CH₃)CON(CH₃)₂ | 83–85 | found | 50.17 | 3.78 | 6.25 | 8.37 | 13.22 |
| | | | | | reqs. | 50.00 | 3.73 | 6.48 | 8.20 | 13.18 |
| 54 | Cl | H | N(C₂H₅)CH₂CH₂OH | | found | 50.44 | 3.99 | 6.92 | 8.76 | 14.08 |
| | | | | | reqs. | 50.27 | 4.10 | 6.89 | 8.86 | 14.18 |
| 55 | Cl | H | N(C₂H₅)CONHCH₃ | 127.5–128.5 | found | 49.51 | 3.91 | 9.95 | 8.64 | 12.60 |
| | | | | | reqs. | 48.87 | 3.62 | 10.06 | 8.49 | 13.64 |
| 56 | Cl | Cl | OC₂H₅ | 100.5–102 | found | 45.26 | 2.43 | 3.36 | 18.00 | 12.33 |
| | | | | | reqs. | 45.47 | 2.54 | 3.54 | 17.90 | 14.39 |
| 57 | Cl | H | OCH(CH₃)CO₂Na | 100–200(d) | found | | | | | |
| | | | | | reqs. | | | | | |
| 58 | Cl | H | OCH(CH₃)CONHC₂H₅ | 133–135 | found | 50.00 | 3.72 | 6.47 | 8.19 | 13.18 |
| | | | | | reqs. | 49.54 | 3.76 | 6.36 | 8.14 | |
| 59 | Cl | H | OCH(C₂H₅)CO₂C₂H₅ | oil | found | | | | | |
| | | | | | reqs. | | | | | |
| 60 | Cl | H | OCH(CH₃)CH₂Cl | oil | found | 47.00 | 2.97 | 3.35 | 17.02 | 13.79 |
| | | | | | reqs. | 46.85 | 2.95 | 3.42 | 17.29 | 13.90 |
| 61 | Cl | H | OCH(CH₃)CH₂OH | oil | found | 49.45 | 3.60 | 3.46 | 9.01 | 14.39 |
| | | | | | reqs. | 49.05 | 3.34 | 3.58 | 9.05 | 14.55 |
| 62 | Cl | H | OCH₂CH₂OCH₃ | 51–52° C | found | 49.16 | 3.48 | 3.35 | 9.37 | 14.14 |
| | | | | | reqs. | 49.06 | 3.34 | 3.58 | 9.05 | 14.55 |
| 63 | Cl | H | OCH(CH₃)CH=CH₂ | oil | found | 52.52 | 3.28 | 3.28 | | 14.92 |
| | | | | | reqs. | 52.6 | 3.4 | 3.54 | | 14.7 |
| 64 | Cl | H | OCH(CH₃)CH—CH₂ (epoxide) | oil | found | 51.24 | 3.30 | 2.81 | | 10.51 |
| | | | | | reqs. | 50.7 | 3.2 | 3.5 | | 14.1 |
| 65 | Cl | H | OSO₂CH₃ | 88–90 | found | 40.91 | 1.99 | 3.27 | 8.67 | 13.20 |

TABLE I-continued
Diphenyl Ethers - Physical Data

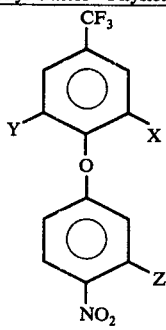

| Example No. | X | Y | Z | m.p. (° C) | | %C | %H | %N | %Cl | %F |
|---|---|---|---|---|---|---|---|---|---|---|
| 66 | Cl | H | OCH(CH$_3$)CO-n-C$_3$H$_7$ | 45–46 | reqs. found | 40.84 | 2.20 | 3.40 | 8.61 | 13.84 |
| 67 | Cl | H | OCH(CH$_3$)CO$_2$-i-C$_3$H$_7$ | 58–59.5 | reqs. found | | | | | |
| 68 | Cl | H | OCH(CH$_3$)CO$_2$CH$_2$CH=CH$_2$ | 61.5–63 | reqs. found | | | | | |
| 69 | Cl | H | OCH(CH$_3$)C(NOH)CH$_3$ | oil | found reqs. | 49.72 48.8 | 3.50 3.4 | 6.21 6.7 | | 13.07 13.6 |

*boiling point

EXAMPLE 3

Preparation of 2-Chloro-α,α,α-trifluoro-p-tolyl-3-ethoxy-4-nitrophenyl ether

Method A a. 1,3-Bis(2-chloro-α,α,α-trifluoro-p-tolyloxy)benzene

A solution of potassium hydroxide (3.26 g. 0.05 mole, 85%) in water (∼ 3 g.) is added slowly dropwise to a solution of resorcinol (2.75 g. 0.025 mole) and 3,4-dichloro-α,α,α-trifluorotoluene (10.75 g. 0.05 mole) in sulfolane (125 ml) at 150°–160° C., with stirring. When the addition is complete, the strongly colored reaction mixture is stirred at 150°–160° C. overnight, then cooled, diluted with benzene (200 ml), and washed cautiously with water (700 ml). Hexane (200 ml) is added and the mixture washed with water (600 ml), dilute sulfuric acid (600 ml), dilute sodium hydroxide solution (600 ml), and water (600 ml), dried, and the solvent removed to give 1,3-bis(2-chloro-α,α,α-trifluoro-p-tolyloxy)benzene (8.6 g. 65%) b.p. 160°–70° C./0.1 mm.

b. 1,3-Bis(2-chloro-α,α,α-trifluoro-p-tolyloxy)-4-nitrobenzene 1,3-Bis(2-chloro-α,α,α-trifluoro-p-tolyloxy)benzene (12 g. 0.0255 mole) is added to a mixture of concentrated nitric acid (12 g.) and sulfuric acid (15 g.) at 5° C. The temperature is then allowed to rise to 25°–30° C with manual stirring and mild ice bath cooling and after 10–20 minutes, the oil solidifies. The mixture is taken up in water/benzene (400 ml)/hexane (400 ml) and the organic phase is washed with water, dried, filtered through activated silica gel (∼ 20 g.), and the solvents removed. The residue is recrystallized from isopropanol to give 1,3-bis(2-chloro-α,α,α-trifluoro-p-tolyloxy)-4-nitrobenzene, (7.4 g. 56%) m.p. 110°–111.5° C.

c. 2-Chloro-α,α,α-trifluoro-p-tolyl-3-ethoxy-4-nitrophenyl ether

A 10% solution of potassium hydroxide in ethanol (10 ml) is added to a solution of 1,3-bis(2-chloro-α,α,α-trifluoro-p-tolyloxy)-4-nitrobenzene (2 g. 0.0039 mole) in dioxane (20 ml). After forty minutes at room temperature, the solution is heated to 45° C for 8 minutes, then cooled, diluted with benzene (50 ml) and hexane (50 ml) and washed with water (3 × 100 ml), dried, and the solvents removed. The residue is recrystallized from isopropanol to give 2-chloro-α,α,α-trifluoro-p-tolyl-3-ethoxy-4-nitrophenylether (1.21 g. 86%) m.p. 83°–84° C.

Method B a. 2-Chloro-α,α,α-trifluoro-p-tolyl-3-hydroxyphenyl ether

A mixture of the di-potassium salt of resorcinol (186.3 g., 1 mol), 3,4-dichloro-α,α,α-trifluorotoluene (53.7 g., 0.25 mol), and sulfolane (100 ml.) is stirred for 30 hours at 140°–160° C.

Benzene (500 ml) and water (200 ml) are added and the organic phase is washed with water (3 × 200 ml), diluted with hexane (500 ml) and washed again with water, dried, filtered through activated silica gel (15 g.), the solvents removed, and the residue distilled to give 2-chloro-α,α,α-trifluoro-p-tolyl-3-hydroxyphenyl ether (45.1 g., 62%) b.p. 112°–124° C./0.3 mm.

b. 2-Chloro-α,α,α-trifluoro-p-tolyl-3-acetoxyphenyl ether

A mixture of 2-chloro-α,α,α-trifluoro-p-tolyl-3-hydroxyphenylether (184 g.) and acetic anhydride (334 g.) is heated on a steam bath for 1 hour and cooled. The mixture is washed with 5% sodium carbonate solution (2 × 500 ml.) and distilled to give 2-chloro-α,α,α-trifluoro-p-tolyl-3-acetoxyphenyl ether (84 g., 40%) b.p. 107°–117° C./0.09 mm.

c. 2-Chloro-α,α,α-trifluoro-p-tolyl-3-acetoxy-4-nitrophenyl ether

A solution of 2-chloro-α,α,α-trifluoro-p-tolyl-3-acetoxyphenyl ether (249 g., 0.75 mol) in 1,2-dichloroethane (1200 ml.) is stirred 2.2 hours at 20°–30° C. with a cooled mixture of concentrated sulfuric acid (276g.) and nitric acid, 70% (227 g.). Hexane (700 ml.) is added and the oil layer washed once with water, 3 times with dilute sodium bicarbonate, and once more with water, dried, filtered through activated silica gel (∼ 40 g.), the solvents removed. The product is crystallized from hexane-benzene to give 2-chloro-α,α,α-trifluoro-p- tolyl-3-acetoxy-4-nitrophenyl ether (207.5 g., 73%)m.p. 83°-89° C.

d. 2-Chloro-α,α,α-trifluoro-p-tolyl-3-hydroxy-4-nitrophenyl ether

A solution of 2-chloro-α,α,α-trifluoro-p-tolyl-3-acetoxy-4-nitrophenyl ether (204.9 g., 0.545 mol) in methanol (2900 ml.) is stirred 1 hour at 20° C. with potassium carbonate (103 g., 0.745 mol). Ninety percent of the methanol is removed; and benzene (1 liter), 7–8% sulfuric acid solution (1600 ml.) are added and stirred 1.5 hours at 25° C. The oil layer is washed twice more with water (200 ml. each), dried, filtered through activated silica gel (40 g.), the solvents removed, and the residue crystallized in hexane to give 2-chloro-α,α,α-trifluoro-p-tolyl-3-hydroxy-4-nitrophenyl ether (165.3 g. 90%)m.p. 68.5°-73° C.

e. 2-Chloro-α,α,α-trifluoro-p-tolyl-3-ethoxy-4-nitrophenyl ether

A solution of 2-chloro-α,α,α-trifluoro-p-trifluoro-p-tolyl-3-hydroxy-4-nitrophenyl ether (60 g., 0.018 mol, 73% pure) and dimethylformamide (100 g.) is converted to the potassium phenoxide and stirred with ethyl bromide (35 g., 0.32 mol) 3 hours at 60° C. and 5 hours at 80° C. Perchlorethylene (150 g.) is added and the solution wahsed twice with water (~ 250 ml. each) at 50° C. The solvents are removed to give 2-chloro-α,α,α-trifluoro-p-tolyl-3-ethoxy-4-nitrophenyl ether (56 g., 83%, 71% pure).

EXAMPLE 7

Preparation of 2-Cyano-α,α,α-trifluoro-p-tolyl-3-ethoxy-4-nitrophenyl ether

A solution of potassium hydroxide (2.6 g., 0.04 mole) 87.3% pure and 3-ethoxy-4-nitrophenol (7.3 g., 0.04 mole) in methanol (30 ml) is stripped to dryness under reduce pressure. A residue of potassium 3-ethoxy-4-nitrophenoxide is dissolved in sulfolane (200 g.) and 4-chloro-3-cyano-benzotrifluoride (8.2 g., 0.04 mole) is added. Gas-liquid chromatography shows the reaction to be complete after stirring at 110° C for 4½ hours and 135° C for 2½ hours. The reaction mixture is cooled and poured into deionized water and the precipitate which forms is filtered off and air dried. Recrystallization from isopropanol yields 2-cyano-α,α,α-trifluoro-p-tolyl-3-ethoxy-4-nitrophenyl ether (7.4 g. 53%) m.p. 143°-145° C.

EXAMPLE 19

Preparation of 2-Chloro-α,α,α-trifluoro-p-tolyl-3-ethylamino-4-nitrophenyl ether A solution of 1,3-bis(2-chloro-α,α,α-trifluoro-p-tolyloxy)-4-nitrobenzene (12.8 g. 0.025 mol), and ethylamine (6.7 g. 0.15 mol) in dioxane (120 ml.) is heated in a pressure bottle 4.5 hours at 50°-55° C. and 4.3 hours at 90°-95° C. Benzene (200 ml.), hexane (70 ml.) and water (500 ml.) are added and the organic phase is washed with water (500 ml.), 10% sodium bicarbonate solution (200 ml.) and water (200 ml.), dried, filtered through activated silica gel (25 g.), the solvents removed, and the residue is crystallized from hexane to give 2-chloro-α,α,α-trifluoro-p-tolyl-3-ethylamino-4-nitrophenyl ether (7.9 g. 88%) m.p. 82°-83° C.

EXAMPLE 21

Preparation of 2-Chloro-α,α,α-trifluoro-p-tolyl-3-diethylamino-4-nitrophenyl ether A solution of 1,3-bis(2-chloro-α,α,α-trifluoro-p-tolyloxy)-4nitrobenzene (12.8 g. 0.025 mol) in p-dioxane (130 ml.) is heated under reflux for 26 hours at 65°-95° C. with diethylamine (50 g. 0.66 mol). Benzene (~ 200 ml.) and water (~ 500 ml.) are added followed by hexane (~ 70 ml.) and the oil layer is separated, washed with water (500 ml), 10% sodium bicarbonate solution (200 ml), and water (200 ml.), dried, filtered through activated silica gel (~ 25 g.), the solvents removed. The residual oil is distilled in vacuo to give 2-chloro-α,α,α-trifluoro-p-tolyl-3-diethylamino-4-nitrophenyl ether (8.15 g 84%) b.p. 180°-190° C./0.01 mm.

EXAMPLE 25

Preparation of 2-Chloro-α,α,α-trifluoro-p-tolyl-3-(1-carboxyethoxy)-4-nitrophenyl ether 2-Chloro-α,α,α-trifluoro-p-tolyl-3-(1-carbethoxyethoxy)-4-nitrophenyl ether (8.6 g. 0.02 mol), potassium hydroxide 86% (2.6 g. 0.04 mol), ethanol (8 ml.), dioxane (8 ml.), and water (100 ml.) are heated at 90°-95° C. for 30 minutes. Ether (200 ml.) and water (200 ml.) are added and the mixture acidified with dilute sulfuric acid, the water layer extracted three times with ether (200 ml. each), dried, and the ether removed to give 2-chloro-α,α,α-trifluoro-p-tolyl-3-(1-carboxyethoxy)-4-nitrophenyl ether (6.4 g. 79%) m.p. 108°-109° C.

EXAMPLE 26

Preparation of 2-Chloro-α,α,α-trifluoro-p-tolyl-3-)1-carbethoxyethoxy)-4-nitrophenyl ether Potassium 2-nitro-5-(2-chloro-α,α,α-trifluoro-p-tolyloxy)phenoxide (7.4 g. 0.02 mol), ethyl 2-bromopropionate (3.6 g. 0.02 mol) and sulfolane (50 ml.) are heated 1.5 hours at 90°-95° C. Benzene (100 ml.) and hexane (100 ml.) are added and the solution is washed with dilute sodium carbonate solution then with water, dried, and the solvent removed. The residue is crystallized from pentane to give 2-chloro-α,α,α-trifluoro-p-tolyl-3-(1-carbethoxyethoxy)-4-nitrophenyl ether (6.2 g., 71%) m.p. 71°-74° C.

EXAMPLE 30

Preparation of 2-Chloro-α,α,α-trifluoro-p-tolyl-3-(1-methyl-2-propynyloxy)-4-nitrophenyl ether This compound is prepared from 1,3-bis(2-chloro-α,α,α-trifluoro-p-tolyloxy)-4-nitrobenzene (289g, 0.565 mole), ethynylmethyl carbinol (100g 1.43 mole) and potassium hydroxide (520 0.80 mole) by the method of Example 3A (c), yielding 206.5 g. of the diphenyl ether as an oil. A separate preparation, carefully purified had m.p. 40°-42° C.

EXAMPLE 32

Preparation of 2-Chloro-α,α,α-trifluoro-p-tolyl-3-(1-acetylethoxy)-4-nitrophenyl ether A mixture of 2-chloro-α,α-p-tolyl-3-(1-methyl-2-propynyloxy)-4-nitrophenyl ether (188.1 g of 90% purity, 0.44 mole), dilute sulfuric acid (8 ml conc. in 190 ml water), mercuric oxide (20g), mercuric chloride (10g), and ethanol (900 ml) are heated under reflux with stirring for 19 hours. The mixture is cooled, the ethanol partially stripped, water is added, and the mixture is filtered and extracted with ether. The extract is filtered through a little activated silica gel and the solvent removed to give an oil (187.1g). On standing, crystals separate and are stirred in hexane and filtered off to give 2-chloro-α,α,α-trifluoro-p-tolyl-3-(1-acetylethoxy)-4-nitrophenyl ether (124 g) as a dark tan solid.

EXAMPLE 37

Preparation of 2-chloro-α,α,α-trifluoro-p-tolyl-3-chloro-4-nitrophenyl ether a. 3-Chloro-4-nitrofluorobenzene m-Chlorofluorobenzene (240 g. 1.85 moles) is added to a mixture of sulfuric acid (185 g. 1.85 moles) and nitric acid (166 g., 1.85 moles) at −5° C. in 3.5 hours, stirred 13 hours, then benzene (200 ml.) and hexane (200 ml.) are added. The extract is washed with water (1 × 300 ml.), sodium carbonate solution (1 × 300 ml.), and water (1 × 300 ml.), dried and the solvents removed. The residue is distilled to give 138 g. of mixed isomers. The 4-nitro isomer crystallizes and is filtered off to give 3-chloro-4-nitrofluorobenzene (51 g. 16.7%) m.p. 36°–38° C.

b. 2-Chloro-α,α,α-trifluoro-p-tolyl-3-chloro-4-nitrophenyl ether

A solution of the potassium phenoxide of 2-chloro-α,α,α-trifluoro-p-cresol (11.7 g, 0.05 mole) in sulfolane (100 ml) is added to a mixture of 3-chloro-4-nitrofluorobenzene (13.1 g, 0.075 mole) and sulfolane (150 ml) in 3.5 hours at 130° C., heated 16 hours at 110° C. and cooled. Benzene (600 ml.) and hexane (400 ml.) are added and the solution washed with water (1 × 500 ml), 5% potassium carbonate (2 × 500 ml), water (2 × 500 ml). The solution is then dired, filtered and solvents are removed. The residue is distilled to give 2-chloro-α,αλ,α-trifluoro-p-tolyl-3-chloro-4-nitrophenyl ether (11.4 g. 65%) b.p. 154°–157° C./0.24 mm.

EXAMPLES 47–49

Preparation of 2-chloro-α,α,α-trifluoro-p-tolyl-3-carbomethoxy-4-nitrophenyl ether a. 3-Cyano-4-nitrofluorobenzene m-Fluorobenzonitrile (96.8 g., 0.8 mole) is added in two and one-half hours to a mixture of concentrated sulfuric acid (600 ml.) and potassium nitrate (80.9 g., 0.8 mole) at 3°–6° C., then allowed to warm to 25° C. The mixture is poured over cracked ice (3000 ml.), extracted with chloroform (5 × 250 ml.), dried and the solvent removed. The residue is extracted with pentane and dried to give 3-cyano-4-nitrofluorobenzene (115 g., 86.5%) m.p. 102°–104° C.

b. 2-Chloro-α,α,α-trifluoro-p-tolyl-3-cyano-4-nitrophenyl ether

The potassium phenoxide of 2-chloro-α,α,α-trifluoro-p-cresol (13.5 g 0.0688 mole) prepared in sulfolane at 5° C. is added to a solution of 3-cyano-4-nitrofluorobenzene (11.4 g., 0.0688 mole) in sulfolane at 120° C. in four hours, stirred 18 hours and cooled. Benzene (200 ml.) and hexane (100 ml) are added and the solution is water washed (5 × 250 ml.), dried, filtered and the solvents removed. The residue is crystallized to give 2-chloro-α,α,α-p-tolyl-3-cyano-4-nitrophenyl ether (16.3 g., 69%) m.p. 95°–103° C. 85% pure.

c. 2-Chloro-α,α,α-trifluoro-p-tolyl-3-carboxy-4-nitrophenyl ether

2-Chloro-α,α,α-trifluoro-p-tolyl-3-cyano-4-nitrophenyl ether (11.2 g. 0.0327 mole), acetic acid (25 ml.), and hydrobromic acid (12 ml. of 47.8% purity) are heated at 120° C., in a pressure bottle, for two days, poured over cracked ice and extracted with benzene (2 × 150 ml). The benzene solution is dried, filtered, the solvent removed, and the residue crystallized from pentane to give 2-chloro-α,α,α-trifluoro-p-tolyl-3-carboxy-4-nitrophenyl ether (7.5 g. 63.5%) m.p. 140°–150° C., 85% pure.

d. 2-Chloro-α,α,α-trifluoro-p-tolyl-3-carbomethoxy-4-nitrophenylether

Hydrogen chloride is bubbled thru a solution of 2-chloro-α,α,α-trifluoro-p-tolyl-3-carboxy-4-nitrophenyl ether (2.3 g., 0.0064 mole) in methanol (50 ml.) for ten hours at 32° C., stirred overnight and the solvent removed to give 2-chloro-α,α,α-trifluoro-p-tolyl-3-carbomethoxy-4-nitrophenyl ether (1.5 g. 40%)

EXAMPLE 48

Preparation of 2-Chloro-α,α,α-trifluoro-p-tolyl-3-carboxy-4-nitrophenyl ether a. 3-(2-Chloro-4-trifluoromethylphenoxy) benzoic acid To a loosely stoppered 500 ml single-necked flask is charged methanol (250 ml) and potassium hydroxide pellets (85%, 13.2 g. 0.20 mole). When the exotherm has subsided and all the potassium hydroxide is in solution, 3-hydroxybenzoic acid (13.8 g. 0.10 mole) is charged rapidly. After stirring for 10 minutes, the methanol is removed in vacuo and the white glossy solid (21.4 g.) is scraped from the flask (in a glove bag through which nitrogen is flowing) and used directly.

To a 300 ml. 3-necked flask fitted with a magnetic stirring bar, condenser, drying tube and thermometer is charged the solid from above dimethylsulfoxide (100 ml), 3,4-dichlorobenzotrifluoride (21.5 g. 0.10 mole) and anhydrous potassium carbonate (5.0 g) to assure an alkaline pH. The reaction temperature is taken rapidly to 138°–44° C while vigorous stirring is maintained. After 4 hours a significant conversion is realized and heating is continued overnight (total 22 hrs.). The reaction mixture is then cooled to room temperature and poured into water (1000 ml) and the aqueous reaction mixture extracted with $CCl_4$ (200 ml). The aqueous layer is then decanted and acidified to pH1 with concentrated hydrochloric acid. The white solid that precipitated is collected by filtration and vacuum dried at 60° C. overnight to give 27 g of an off-white solid 3-(2-chloro-4-trifluoromethylphenoxy)benzoic acid (85% yield), mp 124°–5° C.

b. 2-Chloro-α,α,α-trifluoro-p-tolyl-3-carboxy-4-nitrophenyl ether

Method 1

To a flask is charged concentrated sulfuric acid (40 ml) and ethylene dichloride (25 ml), which is then cooled (ice/salt bath) to 0° C. at which time 3-(2-chloro-4-trifluoromethylphenoxy)benzoic acid (10.0 g. 0.315 mole) is added portion-wise. Then anhydrous potassium nitrate (3.18 g. 0.0315 mole) is added in increments over a ½ hr. period at 0° C. One-half hour after the addition is completed the reaction mixture is allowed to warm gradually to room temperature, the reaction mixture is poured into 400 g. of an ice/water mixture, the aqueous mixture is then extracted with chloroform (2 × 100 ml), the chloroform/water insoluble portion removed by filtration (0.5 g), the chloroform layer decanted and dried over anhydrous sodium sulfate and the solvent removed in vacuo to give 9.4 g of product, mp 137°–50° C., which is recrystallized from benzene/petroleum ether, mp 151.5°–57° C. Anal. Calcd. for $C_{14}H_7ClF_3NO_5$: C, 46.50; H, 1.95; N, 3.87; Cl, 9.80; F, 15.76. Found: C, 46.79; H, 1.91; N, 3.65; Cl, 9.46; F, 15.35.

Method 2

To a 2-liter, 3-necked flask fitted with a stirrer, thermometer and addition funnel is charged methylene chloride (250 ml), 3-(2-chloro-4-trifluoromethylphenoxy)benzoic acid (158 g, 0.500 mole), acetic anhydride (152 g), and then concentrated sulfuric acid (9.8 g). With external cooling, a 70% nitric acid in water solution is added at a rate so as to maintain the reaction temperature at about 20° C. (1 hour period of addition). Then additional acetic anhydride (22.8 g.) is added to the reaction mixture followed by slow addition of more nitric acid (6.8 g). The reaction mixture is then stirred at 20° C. for one hour, poured into two liters of an ice/water mixture and the solid precipitate collected by filtration and vacuum-dried at 60° C. overnight to give 83.4 g. of product, mp 152°–6° C.

EXAMPLES 48A – 48H

Preparation of Salts of 2-Chloro-α,α,α-trifluoro-p-tolyl-3-carboxy-4-nitrophenyl ether The following eight examples show the preparation of representative salts of the invention.

a. Sodium 5-(2-Chloro-4-trifluoromethylphenoxy)-2-nitrobenzoate 5-(2-Chloro-4-trifluoromethylphenoxy)-2-nitrobenzoic acid (1.7 g, 0.0047 mole) is dissolved in methanol (25 ml) and sodium hydroxide (4.7 ml of 1 N NaOH in methanol, 0.0047 mole) is added rapidly. The solvent is then removed in vacuo to give 1.9 g of product that decomposes at 217° C.

b. Dimethylammonium 5-(2-Chloro-4-trifluoromethylphenoxy)-2-nitrobenzoate 5-(2-Chloro-4-trifluoromethylphenoxy)-2-nitrobenzoic acid (2.0 g) is dissolved in toluene and an excess of anhydrous dimethylamine is bubbled into the reaction mixture, the solvent removed in vacuo and the residue triturated with cold diethyl ether to give 1.1 g of product.

c. 2-Ethylhexyl)ammonium 5-(2-Chloro-4-trifluoromethylphenoxy)-2-nitrobenzoate 5-(2-Chloro-4-trifluoromethylphenoxy)-2-nitrobenzoic acid (4.0 g, 0.011 mole) is dissolved in glyme (25 ml) and 2-ethylhexylamine (1.4 g, 0.011 mole) is added rapidly with stirring at room temperature. After a short time the solvent is removed in vacuo to give a semi-solid that is triturated repeatedly with petroleum ether (bp. 30°–60° C) and the solid product (3.1 g) melts at 82°–8° C. Anal. Calcd. for $C_{22}H_{26}ClF_3N_2O_5$: C, 53.83; H, 5.34; N, 5.71; Cl, 7.22; F, 11.61. Found: C, 52.81; H, 5.18; N, 5.98; Cl, 6.70; F, 11.27.

d. Tris-(2-hydroxyethyl)ammonium 5-(2-Chloro-4-trifluoromethylphenoxy)-2-nitrobenzoate 5-(2-Chloro-4-trifluoromethylphenoxy)-2-nitrobenzoic acid (3.0 g, 0.0083 mole) is dissolved in glyme (20 ml) and a solution of triethanolamine (1.35 g, 0.0091 mole) in glyme (5 ml) is added rapidly while stirring at room temperature. After stirring for a few hours the solvent is removed in vacuo, the product is triturated repeatedly with petroleum ether (bp 30°–60° C.) and dried to a weight of 2.5 g. Anal. Calcd. for $C_{20}H_{22}ClF_3N_2O_8$: C, 47.02; H, 4.34; Cl, 6.39; N, 5.48; F, 11.15. Found: C, 47.08; H, 4.78; Cl, 6.48; N, 5.21; F, 10.16.

e. Dicyclohexylammonium 5-(2-Chloro-4-trifluoromethylphenoxy)-2-nitrobenzoate 5-(2-Chloro-4-trifluoromethylphenoxy)-2-nitrobenzoic acid (3.0 g, 0.0083 mole) is dissolved in glyme (20 ml) and dicyclohexylamine (1.64 g, 0.0091 mole) is added at room temperature while stirring. The solvent is removed in vacuo, the residue triturated with petroleum ether (bp 30°–60° C.) and dried to give 2.7 g of product, mp 197°–9° C. Anal. Calcd. for $C_{26}H_{30}ClF_3N_2O_5$: C, 57.51; H, 5.56; N, 5.15; Cl, 6.53; F, 10.49. Found: C, 57.25; H, 5.71; N, 5.55, Cl, 6.40; F, 10.24.

f. t-Octylammonium 5-(2-Chloro-4-trifluoromethylphenoxy)-2-nitrobenzoate 5-(2-Chloro-4-trifluoromethylphenoxy)-2-nitrobenzoic acid (3.0 g, 0.0083 mole) is dissolved in glyme (20 ml) and t-octylamine (1.17 g, 0.0091 mole) is added rapidly while stirring. The solvent is removed in vacuo and the residue triturated with petroleum either (bp 30°–60° C.) and dried to give 2.8 g of product, mp 140°–57° C. Anal. Calcd. for $C_{22}H_{24}ClF_3N_2O_5$: C, 53.82; H, 5.33; N, 5.70; Cl, 7.22; F, 11.61. Found: C, 53.50; H, 5.37; N, 6.06; Cl, 6.87; F, 11.10.

g. 2-Hydroxyethylammonium 5-(2-Chloro-4-trifluoromethylphenoxy)-2-nitrobenzoate

A 20% aqueous solution of the salt is prepared by pulvering 5-(2-chloro-4-trifluoromethyl(pehnoxy)-2-nitrobenzoic acid (22.2 g, 90% pure) and slurrying it in water (62.8 g). To this is added ethanolamine (4.0 g, 10% purity) until a resultant pH of 8.0 is obtained. The slurry is then diluted further with water (11 g) to give the desired aqueous concentration.

Similarly prepared (using the proper amine or metal hydroxide) are aqueous solutions of the following salts of 5-(2-chloro-4-trifluoromethylphenoxy)-2-nitrobenzoic acid:

Bis-(2-hydroxyethyl)ammonium salt
Tris-(2-hydroxyethyl)ammonium salt
Sodium salt
Potassium salt h. Benzyltrimethylammonium 5-(2-Chloro-4-trifluoromethylphenoxy)-2-nitrobenzoate A 20% aqueous methanolic solution of the salt is prepared by slurrying 5-(2-chloro-4-trifluoromethylphenoxy)-2-nitrobenzoic acid (22.2 g, 90% pure) in water (50 g) and adding a 40% solution of benzyltrimethylammonium methoxide (27 g) in methanol to pH 8. Additional water (0.8 g) is then added to give the desired concentration.

EXAMPLE 51

Preparation of 2-chloro-α,α,α-trifluoro-p-tolyl-3-(1-carbamoylethoxy)-4-nitrophenyl ether a. 2-Chloro-α,α,α-trifluoro-p-tolyl-3-(1-chloroformylethoxy)-4-nitrophenyl ether 2-Chloro-α,α,α-trifluoro-p-tolyl-3-(1-carboxyethoxy)-4-nitrophenyl ether (34.8 g. 0.086 mol), thionyl chloride (20.4 g. 0.172 mol), and benzene (150 ml) are stirred 5 hours at 90° C. and sixteen hours at 25° C. The benzene is removed to give 2-chloro-α,α,α-trifluoro-p-tolyl-3-(1-chloroformylethoxy)-4-nitrophenyl ether (33.4 g. 92%).

b. 2-Chloro-α,α,α-trifluoro-p-tolyl-3-(1-carbamoylethoxy)-4-nitrophenyl ether

A solution of 2-chloro-α,α,α-trifluoro-p-tolyl-3-(1-chloroformylethoxy)-4-nitrophenyl ether (4.2 g. 0.01 mol) in ether (50 ml.) is added to an ether solution (200 ml.) saturated with gaseous ammonia at zero temperatures. After 30 minutes, water (100 ml.) is added and the ether layer separated. The aqueous phase is extracted with ether (3 × 200 ml.) and the combine extracts dried, filtered through activated silica gel (20 g.), and the solvent removed to give 2-chloro-α,α,α-trifluoro-p-tolyl-3-(1-carbamoylethoxy)-4-nitrophenyl ether (2.4 g. 60%) m.p. 108°-111° C.

EXAMPLE 55

Preparation of
2-Chloro-α,α,α-trifluoro-p-tolyl-3-(3-methyl-1-ethylureido)-4-nitrophenyl ether a. 2-Chloro-α,α,α-trifluoro-p-tolyl-3-(n-ethylchloroformamido)-4-nitrophenyl ether A mixture of 2-chloro-,α,α,α-trifluoro-p-tolyl-3-ethylamino-4-nitro phenyl ether (3.6 g. 0.01 mol), phosgene (18.9 g. 0.19 mol), 2,6-lutidine (2.2 g. 0.02 mol), and benzene (~130 ml.) are heated in a pressure bottle 64 hours at 90°-95° C. The mixture is cooled, filtered and the solvent removed to give 2-chloro-α,α,α-trifluoro-p-tolyl-3-(N-ethylchloroformamido)-4-nitrophenyl ether.

b. 2-Chloro-α,α,α-trifluoro-p-tolyl-3-3-methyl-1-ethylureido)-4-nitrophenyl ether A solution of 2-chloro-α,α,α-trifluoro-p-tolyl-3-(N-ethylchloroformamide)-4-nitrophenyl ether (4.4 g., 0.01 mol), methylamine (3.3 g 0.11 mol) and benzene (~60 ml.) is allowed to stand 25 minutes at 0° C., filtered, and the solvent removed. Benzene (~100 ml.) and hexane (50 ml.) are added and the solution is washed with water (100 ml.) and aqueous 10% sodium carbonate solution (2 × 100 ml.), dried, and the product absorbed on activated silica gel (~25 g.). The product is eluted with a mixture of benzene (400 ml.) and methanol (40 ml) the solvents removed and the product recrystallized to give 2-chloro-α,α,α-trifluoro-p-tolyl-3-(3-methyl-1-ethylureido)-4-nitrophenyl ether (2.6 g. 62%) m.p. 127.5°-128.5° C.

EXAMPLE 56

Preparation of
2,6-Dichloro-α,α,α-trifluoro-p-tolyl-3-ethoxy-4-nitrophenyl ether a. 3,4-Dichloro-5-nitro-α,α,α-trifluorotoluene 3,4-Dichloro-α,α,α-trifluorotoluene (862 g. 4.0 mols) is added to a stirred mixture of concentrated sulfuric acid (4400 g.) and nitric acid (3400 g.) at 35° C. The mixture is stirred 70 minutes at 95° C. and allowed to separate. The oil layer is washed once with water and twice with 5% sodium carbonate solution, dried, and fractionally distilled to give 3,4-dichloro-5-nitro-α,α,α-trifluorotoluene (188 g. 18%) b.p. 115°-118° C./15 mm, 88% pure.

b. 5-Amino-3,4-dichloro-α,α,α-trifluorotoluene 500 ml. of an ethanolic solution containing 3,4-dichloro-5-nitro-α,α,α-trifluorotoluene (188 g. 0.72 mol), and platinum oxide (Adam's catalyst) (0.2 g.) is reduced at room temperature in a low pressure hydrogenation apparatus to give 5-Amino-3,4-dichloro-α,α,α-trifluorotoluene (129.9 g. 78%) b.p. 65°-70° C./1-2 mm.

c. 3,4,5-Trichloro-α,α,α-trifluorotoluene

A solution of sodium nitrite (39 g.) in water (85 ml.) is added over 1 hour to a solution of 5-amino-3,4-dichloro-α,α,α-trifluorotoluene (117.5 g., 0.51 mol) in 1700 ml. concentrated hydrochloric acid at −6° C. and the solution stirred for 1 hour then filtered. The filtrate is added to a solution of cuprous chloride (76.5 g.) in concentrated hydrochloric acid (500 ml.) over 5 minutes at 0° to 8° C. and gradually heated to 80° C. over 80 minutes. The reaction mixture is cooled to 35° C. and extracted with hexane (2 × 300 ml.). The extract is washed with water, 2% sodium hydroxide solution, dried and distilled to give 3,4,5-trichloro-α,α,α--trifluorotoluene (70 g., 55%) b.p. 82°-86° C./10 mm, 95% pure.

d. 1,3-Bis(2,6-dichloro-α,α,α-trifluoro-p-tolyloxy)-benzene

A mixture of 3,4,5-trichloro-α,α,α-trifluorotoluene (10 g. 0.04 mol), and the dipotassium salt of 1,3-dihydroxybenzene (4 g. 0.021 mol) in 150 ml. sulfolane is stirred and heated 70 minutes at ~120° C. The cooled reaction mixture is diluted with benzene (350 ml.) and washed once with water (1 l). Hexane (200 ml.) is added, and the solution washed with water (3 × 500 ml.) dried, filtered through activated silica gel (~25 g.), and the solvents removed. The residual oil is crystalized from a mixture of pentane and benzene to give 1,3-bis(2,6-dichloro-α,α,α-trifluoro-p-tolyloxy)benzene (5.3 g. 49%) m.p. 121°-122° C.

e. 1,3-Bis(2,6-dichloro-α,α,α-trifluoro-p-tolyloxy)-4-nitrobenzene

A cooled mixture of concentrated sulfuric acid (6.5 ml.) and nitric acid (4.4 ml.) is added with stirring to an ice cold solution of 1,3-bis(2,6-dichloro-α,α,α-trifluoro-p-tolyloxy)-benzene (11.1 g. 0.021 mol) in 1,2-dichloroethane (30 ml.). After thirty minutes at room temperature, the phases are allowed to separate and the organic phase washed twice with water. Benzene (200 ml.) is added and the solution washed twice with dilute sodium carbonate solution, dried, filtered through activated silica gel (~25 g.), and the solvents removed. The residual crystals are triturated with pentane, filtered, and dried to obtain 1,3-bis(2,6-dichloro-α,α,α-trifluoro-p-tolyloxy)-4-nitrobenzene (9.9 g., 82%) m.p. 137.5°-140.5° C., 90% pure.

f. 2,6-Dichloro-α,α,α-trifluoro-p-tolyl-3-ethoxy-4-nitrophenyl ether

A solution of potassium hydroxide, 86% (1.9 g., 0.029 mol) in ethanol (20 ml.) is added to a solution of 1,3-bis(2,6-dichloro-α,α,α-trifluoro-p-tolyloxy)-4-nitrobenzene (8.0 g., 0.014 mol) in p-dioxane (70 ml.) and warmed 1 hour at 50° C. The solution is cooled and benzene (~250 ml.) is added and crystals of potassium 2-nitro-5-(2,6-dichloro-α,α,α-trifluoro-p-tolyloxy)-phenoxide (2.9 g. 52%) are collected. Treatment with acid yields the free phenol, 2,6-dichloro-α,α,α-trifluoro-p-tolyl-3-hydroxy-4-nitrophenyl ether (2.0 g. 40%) m.p. 84.5°-86.5° C. This phenol (1.7 g. 0.0046 mol) is reconverted to the potassium salt, dissolved in dimethylformamide (20 ml.) and treated with ethyl iodide (1.2 g. 0.0077 mol) 2.5 hours at 50°-70° C. The reaction mixture is diluted with benzene (100 ml.) and hexane (50 ml.), washed with water (3 × 100 ml.), dried, filtered through activated silica gel (15 g.), and the solvents removed to give 2,6-dichloro-α,α,α-trifluoro-p-tolyl-3- ethoxy-4-nitrophenyl ether (0.8 g. 44%) m.p. 100.5°–102° C.

From the filtrate of the 2.9 g. of phenoxide there is recovered ethyl 2,6-dichloro-α,α,α-trifluoro-p-tolyl ether (3.0 g. 82%) b.p. 78° C./5 mm, and an additional amount of the product 2,6-dichloro-α,α,α-trifluoro-p-tolyl-3-ethoxy-4-nitrophenyl ether (0.35 g. 6%) m.p. 88°–93° C.

EXAMPLE 58

Preparation of 2-chloro-α,α,α-trifluoro-p-tolyl-3-(1-N-ethyl-carbamoylethoxy)-4-nitrophenyl ether The potassium salt of 2-chloro-α,α,α-trifluoro-p-tolyl-3-hydroxy-4-nitrophenyl ether (see Example 3, Method B, part d above), which is prepared by combining the subject hydroxy compound with a basic potassium salt (e.g., potassium carbonate, potassium hydroxide, etc.) in a number of suitable solvents, is dissolved in sulfolane (50 ml) and a solution of N-ethyl-2-chloropropionamide (1.4 g, 0.010 mole) in sulfolane (10 ml) is then charged. The combined reaction mixture is then heated overnight at 115° C, cooled, poured into water and extracted with carbon tetrachloride. The dried (anh. MgSO$_4$) carbon tetrachloride layer is then reduced in vacuo to give a yellow oil that solidifies upon trituration with pentane, 3.2 g, m.p. 133°–5° C.

EXAMPLE 59

Preparation of 2-chloro-α,α,α-trifluoro-p-tolyl-3-(1-carbethoxypropoxy)-4-nitrophenyl ether To a 500 ml, 3-necked flask fitted with a condenser, drying tube, stirrer and thermometer is charged 2-chloro-α,α,α-trifluoro-p-tolyl-3-hydroxy-4-nitrophenyl ether (10 g, 0.30 mole), anhydrous potassium carbonate (6.25 g, 0.045 mole), dimethylsulfoxide (100 ml) and ethyl α-bromo-n-butyrate (5.8 g, 0.030 mole) and the reaction mixture heated overnight at 65° C, cooled, and poured into water (550 ml) and extracted twice with methylene chloride (2 × 200 ml). The combined methylene chloride extracts were washed (250 ml H$_2$O) and the organic layer dried (anh. Na$_2$SO$_4$) and the solvent removed in vacuo (0.2 mm at 90° C, overnight) to give 11.9 g of yellow, oily product.

EXAMPLE 61

Preparation of 2-chloro-α,α,α-trifluoro-p-tolyl-3-(1-hydroxymethylethoxy)-4-nitrophenyl ether A solution of 2-chloro-α,α,α-trifluoro-p-tolyl-3-(1-carbethoxyethoxy)-4-nitrophenyl ether (17.32 g, 0.04 mole) in dry ether (500 ml) is treated at −10° C with a suspension of lithium aluminum hydride (1.9 g) in ether (approximately 100 ml) added with stirring over ten seconds. The termperature increases to about 0° to 10° C and after a total of 45 seconds, the reaction mixture is quenched by pouring, with stirring, onto ice/dilute sulfuric acid. The ether phase is washed with water, dried, filtered through activated silica gel, and the solvent removed to give 2-chloro-α,α,α-trifluoro-p-tolyl-3-(1-hydroxymethylethoxy)-4-nitrophenyl ether as a dark oil, yield 14 g.

EXAMPLE 60

Preparation of 2-chloro-α,α,α-trifluoro-p-tolyl-3-(1-chloromethylethoxy)-4-nitrophenyl ether 2-Chloro-α,α,α-trifluoro-p-tolyl-3-(1-hydroxymethylethoxy)-4-nitrophenyl ether (3.92 g, 10 mmole) is dissolved in benzene (approximately 6 ml) and heated at 40° C overnight in the presence of thionyl chloride (3.6 g 30 mmole) and pyridine (1 drop). After cooling, the solution is diluted with methylene dichloride, washed with warer, dried, filtered through activated silica gel, and the solvent stripped to give 2-chloro-α,α,α-trifluoro-p-tolyl-3-(1-chloromethylethoxy)-4-nitrophenyl ether as a yellow oil, yield 4 g.

EXAMPLES 70 to 85

Following the procedures of Examples 1 to 69, and conventional procedures well-known to those skilled in the art, other diphenyl ethers of Formula I are prepared. Among the compounds which are prepared by these procedures are:

α,α,α,α',α',α'-hexafluoro-2,4-xylyl-3-ethoxy-4-nitrophenyl ether

α$^4$,α$^4$,α$^4$-trifluoro-2,4-xylyl-3-n-propoxy-4-nitrophenyl ether, 2-chloro-6,α,α,α-tetrafluoro-p-tolyl-3-ethyl-4-nitrophenyl ether, 2-iodo-α,α,α-trifluoro-p-tolyl-3-methoxy-4-nitrophenyl ether, 2-chloro-6-cyano-α,α,α-trifluoro-p-tolyl-3-methylthio-4-nitrophenyl ether, 2-bromo-α,$^4$α,$^4$α$^4$-trifluoro-4,6-xylyl-3-ethoxy-4-nitrophenyl ether, 2-chloro-α,α,α,α',α',α'-hexafluoro-4,6-xylyl-3-methoxy-4-nitrophenyl ether, 2-bromo-α,α,α-trifluoro-p-tolyl-3-ethoxy-4-nitrophenyl ether, 2-chloro-α,α,α-trifluoro-p-tolyl-3-n-butyl-4-nitrophenyl ether, 2-chloro-α,α,α-trifluoro-p-tolyl-3-bromo-4-nitrophenyl ether, 2-cyano-α,α,α-trifluoro-p-tolyl-3-acetoxy-4-nitrophenyl ether, 2-bromo-α,α,α-trifluoro-p-tolyl-3-diethylamino-4-nitrophenyl ether, 2,6-dichloro-α,α,α-trifluoro-p-tolyl-3-ethylamino-4-nitrophenyl ether, 2-cyano-α,α,α-trifluoro-p-tolyl-3-(1-carbethoxyethoxy)-4-nitrophenol ether, 2-cyano-α,α,α-trifluoro-p-tolyl-3-carbomethoxy-4-nitrophenyl ether, and 2-bromo-α,α,α-trifluoro-p-tolyl-3-carboxy-4-nitrophenyl ether.

It should be noted that the diphenyl ethers of the invention can also be named correctly using different systems of nomenclature. For example, the diphenyl ether of Example 3 can also be named as 2-cyano-4-trifluoromethyl-3'-ethoxy-4'-nitrodiphenyl ether. However, within the specification and claims of this invention the system of nomenclature exemplified in Examples 1 to 85 has been followed.

The following examples show the herbicidal properties of the diphenyl ethers of the invention.

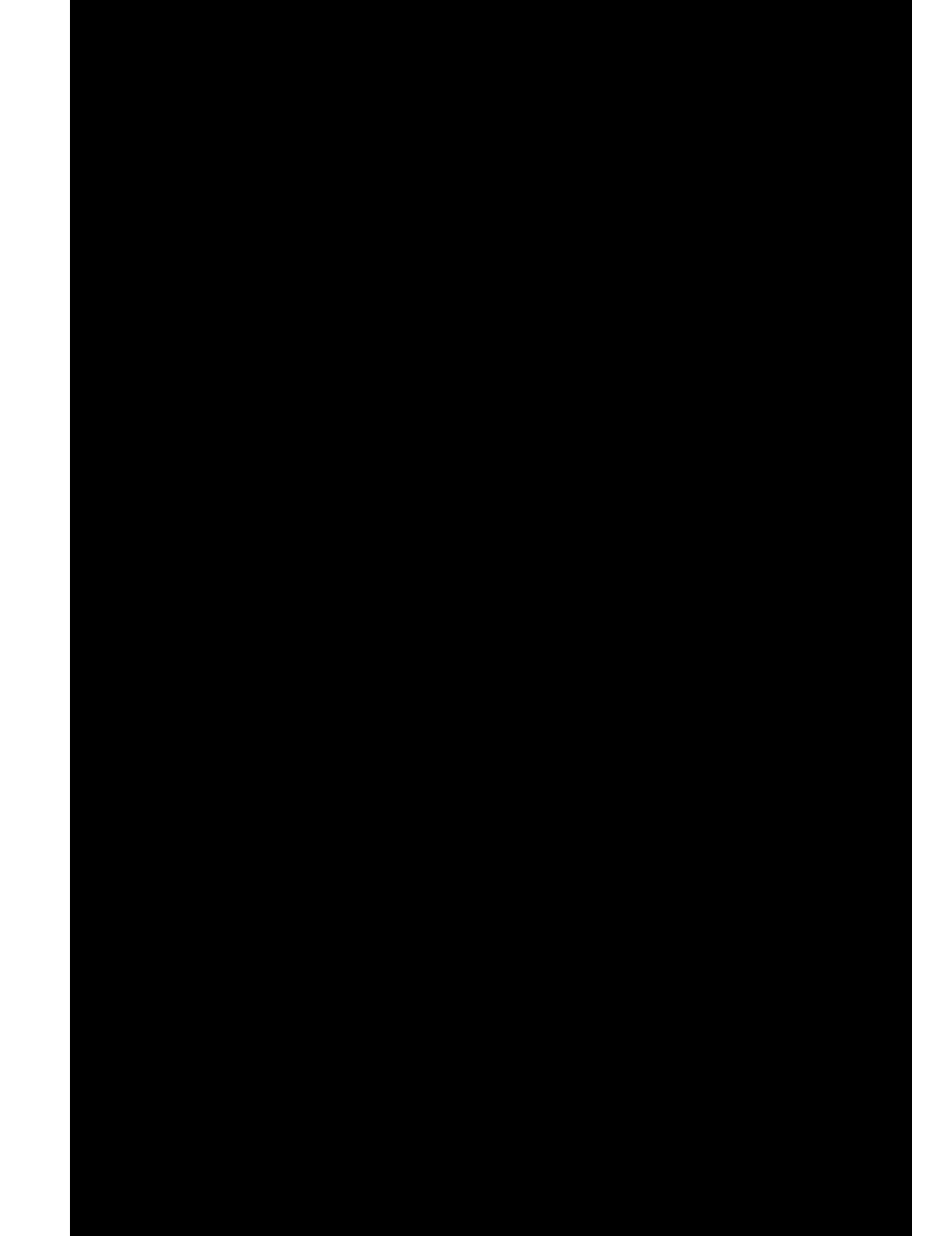

TABLE II-continued
HERBICIDAL ACTIVITY
(% control)

| | | | | | |
|---|---|---|---|---|---|
| 42 | M | 62 | 83 | 38 | 63 |
| | D | 80 | 60 | 98 | 88 |
| 43 | M | 0 | 99 | 2 | 61 |
| | D | 48 | 100 | 47 | 80 |
| 44 | M | 66 | 0 | 60 | 7 |
| | D | 96 | 17 | 98 | 10 |
| 45 | M | 13 | 68 | 17 | 53 |
| | D | 58 | 77 | 88 | 78 |
| 46 | M | 0 | 34 | 0 | 0 |
| | D | 20 | 87 | 30 | 4 |
| 47 | M | 61 | 80 | 11 | 24 |
| | D | 40 | 80 | 72 | 84 |
| 48 | M | 99 | 100 | 75 | 84 |
| | D | 97 | 100 | 100 | 97 |
| 49 | M | 92 | 100 | 86 | 77 |
| | | 95 | 100 | 100 | 100 |
| 50 | M | 90 | 98 | 97 | 100 |
| | D | 83 | 100 | 100 | 100 |
| 51 | M* | 79 | 96 | 75 | 86 |
| | D* | 100 | 100 | 100 | 98 |
| 52 | M | 79 | 98 | 87 | 93 |
| | D | 67 | 75 | 100 | 100 |
| 53 | M | 98 | 98 | 79 | 81 |
| | D | 83 | 100 | 100 | 100 |
| 54 | M | 83 | 98 | 79 | 71 |
| | D | 75 | 98 | 100 | 100 |
| 55 | M | 91 | | 69 | 31 |
| | D | 73 | | 95 | 96 |
| 56 | M | 91 | 100 | 99 | 100 |
| | D | 83 | 100 | 100 | 99 |
| 57 | M | 94** | 86 | 68 | 79 |
| | D | 93** | 86 | 86 | 100 |
| 58 | M | | | 37 | 7 |
| | D | | | 34 | 70 |
| 59 | M | | | 60 | 71 |
| | D | | | 80 | 100 |
| 60 | M | | | 83 | 86 |
| | D | | | 55 | 100 |
| 61 | M | | | 70 | 93 |
| | D | | | 54 | 100 |
| 62 | M | 95 | 95 | 85 | 92 |
| | D | 97 | 94 | 87 | 87 |

*M = Monocots; D = Dicots
**8 lb./A.

EXAMPLE 87

This example shows the selective herbicidal activity of diphenyl ethers of the invention in a number of agronomic crops. Following the general test procedure of Example 86, diphenyl ethers are evaluated for significant tolerance (as shown by 50% or less kill of the test crop at levels of application which give more than 50% kill of many or all of the weeds of Example 86) towards some or all of the following common agronomic crops (not all compounds tested against all crops): alfalfa, snapbeans, corn, cotton, cucumbers, peanuts, rape, rice, safflower, soybeans, tomatoes, and wheat.

Tolerance to snapbeans in preemergence applications is shown by the compounds of Examples 4 and 26. Tolerance to corn in preemergence application is shown by the compounds of Examples 4, 11, 19, 21, 34, 40, 52, and 54 and in postemergence applications by the compounds of Examples 4, 18, 19, 21, 26, 34, 36, 40, 49, 52, 53, 54, and 56. Tolerance to cotton in preemergence applications is shown by the compounds of Examples 3, 4, and 30 and in postemergence or layby applications by the compound of Example 3. Tolerance to peanuts in preemergence applications is shown by the compounds of Examples 3, 19, 21, 30, 34, 36, 40, 48, 49, 50, 52, 53, and 56 and in postemergence applications by the compounds of Examples 4, 18, 34, 36, 37, 40, 48, 53, and 54. Tolerance to rice in preemergence applications is shown by the compounds of Examples 4, 19, 21, 30, 34, 40, 52, and 54 and in postemergence applications or in applications on transplanted rice by the compounds of Examples 3, 11, 18, 20, 30, 34, 40, 48, 53, and 54. Tolerance to safflower in preemergence applications is shown by the compound of Example 3. Tolerance to soybeans in preemergence applications is shown by the compounds of Examples 3, 4, 11, 18, 19, 21, 26, 30, 34, 40, 48, 49, 50, 52, 53, and 54, and salts of Examples 48(a) to (h), and in postemergence or layby applications by the compounds of Examples 3 and 34. Tolerance to wheat in preemergence applications is shown by the compounds of Examples 4, 18, 19, 26, 34, 40, 50, 54, and 56 and in postemergence applications by the compounds of Examples 4, 18, 21, 30, 34, 36, 48, and 54.

It is to be understood that changes and variations may be made without departing from the spirit and scope of the invention as defined by the appended claims.

We claim:

1. A compound of the formula

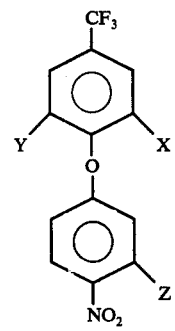

wherein
X is a hydrogen atom, a halogen atom, a trifluoromethyl group, or a ($C_1$–$C_4$) alkyl group, T is a hydrogen atom, a halogen atom, or a trifluoromethyl group, and Z is a ($C_1$–$C_4$) alkoxy group having one or more hydrogen atoms replaced by a carboxy group, or an agronomically-acceptable salt thereof, or a carb($C_1$–$C_4$)alkoxy group.

2. A compound according to claim 1 wherein Z is a group of the formula

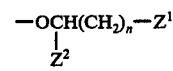

wherein
$Z^1$ is a carboxy group, or an agronomically-acceptable salt thereof, or a carb($C_1$–$C_4$)alkoxy group, $Z^2$ is a hydrogen atom or a ($C_1$–$C_3$)alkyl group, and n is 0 or 1.

3. A compound according to claim 1 wherein Y is a hydrogen atom.

4. A compound according to claim 3 wherein X is a halogen atom.

5. A compound according to claim 2 wherein $Z^2$ is a methyl group and n is 0.

6. A compound according to claim 5 wherein $Z^1$ is a carb($C_1$–$C_4$)alkoxy group.

7. A compound according to claim 6 wherein X is a chlorine atom and $Z^1$ is a carbethoxy group.

8. A compound according to claim 5 wherein $Z^1$ is a carboxy group or an agronomically-acceptable salt thereof.

9. A compound according to claim 8 wherein X is a chlorine atom.

10. A herbicidal composition which comprises a herbicidally effective amount of a compound according to claim 1 and an agronomically-acceptable carrier.

11. A composition according to claim 10 which also comprises a surfactant.

12. A method of controlling weeds which comprises applying to the surface of the growth medium prior to the emergence of the weeds from the growth medium a compound according to claim 1 in an amount sufficient to control the growth of the weeds.

13. The method of claim 12 wherein the compound is applied at a rate of about 0.1 to about 12 pounds per acre.

14. A method of controlling weeds which comprises applying to weed seedlings a compound according to claim 1 in an amount sufficient to control the growth of the seedlings.

15. The method of claim 14 wherein the compound is applied at a rate of about 0.1 to about 12 pounds per acre.

* * * * *

UNITED STATES PATENT AND TRADEMARK OFFICE
Certificate

Patent No. 4,093,446                                                             Patented June 6, 1978

Horst O. Bayer, Colin Swithenbank & Roy Y. Yih

Application having been made by Horst O. Bayer, Colin Swithenbank & Roy Y. Yih, the inventors named in the patent above identified, and Rohm and Haas Co., Philadelphia, Pa., a Corp. of Delaware, the assignee, for the issuance of a certificate under the provisions of Title 35, Section 256, of the United States Code, deleting the name of Roy Y. Yih as a joint inventor, and a showing and proof of facts satisfying the requirements of the said section having been submitted, it is this 23rd day of Aug. 1983, certified that the name of the said Roy Y. Yih is hereby deleted from the said patent as a joint inventor with the said Horst O. Bayer & Colin Swithenbank.

Fred W. Sherling,
*Associate Solicitor*